(12) United States Patent
Mishima et al.

(10) Patent No.: US 7,666,173 B2
(45) Date of Patent: Feb. 23, 2010

(54) DISPOSABLE WEARING ARTICLE HAVING A TRANSVERSE PARTITION

(75) Inventors: Yoshitaka Mishima, Kagawa-ken (JP); Kaiyo Nakajima, Kagawa-ken (JP)

(73) Assignee: Uni-Charm Corporation, Shikokuchuo-Shi, Ehime-Ken (JP)

( * ) Notice: Subject to any disclaimer, the term of this patent is extended or adjusted under 35 U.S.C. 154(b) by 333 days.

(21) Appl. No.: 11/138,338

(22) Filed: May 27, 2005

(65) Prior Publication Data
US 2005/0267436 A1 Dec. 1, 2005

(30) Foreign Application Priority Data
May 31, 2004 (JP) .............................. 2004-160757

(51) Int. Cl.
 *A61F 13/494* (2006.01)
 *A61F 13/495* (2006.01)
(52) U.S. Cl. ........................... 604/385.19; 604/385.28; 604/385.101
(58) Field of Classification Search ............ 604/385.19, 604/385.27, 385.08, 385.09, 385.28, 385.29, 604/401, 402, 385.101
See application file for complete search history.

(56) References Cited

U.S. PATENT DOCUMENTS

| | | | | |
|---|---|---|---|---|
| RE26,151 E | * | 1/1967 | Duncan et al. | 604/375 |
| 3,848,599 A | | 11/1974 | Schaar | |
| 3,860,003 A | * | 1/1975 | Buell | 604/385.25 |
| 4,490,147 A | * | 12/1984 | Pierce et al. | 604/378 |
| 4,573,990 A | * | 3/1986 | Ohsaki | 604/385.201 |
| 4,662,877 A | * | 5/1987 | Williams | 604/385.27 |
| 4,695,278 A | * | 9/1987 | Lawson | 604/385.27 |
| 4,753,646 A | * | 6/1988 | Enloe | 604/385.29 |
| 4,795,453 A | * | 1/1989 | Wolfe | 604/385.101 |
| 4,892,536 A | * | 1/1990 | DesMarais et al. | 604/385.27 |
| 4,909,803 A | * | 3/1990 | Aziz et al. | 604/385.28 |
| 5,151,092 A | * | 9/1992 | Buell et al. | 604/385.3 |
| 5,171,236 A | * | 12/1992 | Dreier et al. | 604/369 |
| 5,306,266 A | * | 4/1994 | Freeland | 604/385.19 |
| 5,342,337 A | * | 8/1994 | Runeman et al. | 604/378 |
| 5,342,342 A | * | 8/1994 | Kitaoka | 604/385.19 |
| 5,514,121 A | * | 5/1996 | Roe et al. | 604/385.19 |
| 5,527,300 A | * | 6/1996 | Sauer | 604/378 |

(Continued)

FOREIGN PATENT DOCUMENTS

EP 0 908 162 A2 4/1999

(Continued)

OTHER PUBLICATIONS

European Search Report for 05745617 issued Nov. 14, 2007.

*Primary Examiner*—Tatyana Zalukaeva
*Assistant Examiner*—Paula L Craig
(74) *Attorney, Agent, or Firm*—Lowe Hauptman Ham & Berner

(57) ABSTRACT

A disposable wearing article includes a partition provided in a front half of a crotch region divided by a transverse centerline bisecting a longitudinal dimension of the article so that the partition extends in the transverse direction on a topsheet. During use of the article, the partition curves in the transverse direction so as to describe a generally circular arc which is convex upward above the topsheet. The partition is thus spaced upward from the topsheet and the wearer's genital organ in contact with an outer surface of the partition is also spaced from the topsheet. In this way, the genital organ is protected from soiling with loose passage.

1 Claim, 20 Drawing Sheets

U.S. PATENT DOCUMENTS

| | | | | |
|---|---|---|---|---|
| 5,527,302 | A * | 6/1996 | Endres et al. | 604/385.21 |
| 5,558,661 | A * | 9/1996 | Roe et al. | 604/385.19 |
| 5,576,091 | A * | 11/1996 | Zajaczkowski et al. | 428/192 |
| 5,683,374 | A * | 11/1997 | Yamamoto et al. | 604/385.29 |
| 5,779,690 | A * | 7/1998 | Gustafsson et al. | 604/385.19 |
| 5,810,799 | A | 9/1998 | Slater | |
| 5,817,086 | A * | 10/1998 | Kling | 604/385.19 |
| 5,853,403 | A * | 12/1998 | Tanzer et al. | 604/385.09 |
| 6,010,490 | A * | 1/2000 | Freeland et al. | 604/385.19 |
| 6,123,692 | A * | 9/2000 | Guidotti et al. | 604/385.01 |
| 6,133,501 | A * | 10/2000 | Hallock et al. | 604/369 |
| 6,152,907 | A * | 11/2000 | Widlund et al. | 604/385.08 |
| 6,159,191 | A * | 12/2000 | Mishima et al. | 604/385.28 |
| 6,168,584 | B1 * | 1/2001 | Allen et al. | 604/385.19 |
| 6,179,820 | B1 * | 1/2001 | Fernfors | 604/385.27 |
| 6,222,092 | B1 * | 4/2001 | Hansen et al. | 604/378 |
| 6,248,098 | B1 * | 6/2001 | Sayama | 604/385.28 |
| 6,383,170 | B1 * | 5/2002 | Mishima et al. | 604/385.19 |
| 6,410,822 | B1 * | 6/2002 | Mizutani | 604/380 |
| 6,464,676 | B2 * | 10/2002 | Mishima | 604/385.19 |
| 6,471,682 | B2 | 10/2002 | Kashiwagi | |
| 6,475,199 | B1 * | 11/2002 | Gann et al. | 604/385.01 |
| 6,506,185 | B1 | 1/2003 | Sauer et al. | |
| 6,527,756 | B1 * | 3/2003 | Mishima et al. | 604/385.19 |
| 6,530,091 | B2 * | 3/2003 | Takai et al. | 2/406 |
| 6,570,056 | B1 * | 5/2003 | Tanzer et al. | 604/368 |
| 6,638,260 | B2 * | 10/2003 | Mishima | 604/385.19 |
| 6,699,228 | B1 * | 3/2004 | Chmielewski et al. | 604/385.28 |
| 6,786,895 | B1 * | 9/2004 | Schmitz | 604/385.28 |
| 6,869,423 | B2 * | 3/2005 | Onishi et al. | 604/385.01 |
| 6,921,394 | B2 * | 7/2005 | Sayama et al. | 604/385.19 |
| 7,204,830 | B2 * | 4/2007 | Mishima et al. | 604/385.19 |
| 7,238,175 | B2 * | 7/2007 | Onishi et al. | 604/385.24 |
| 7,470,264 | B2 * | 12/2008 | Mishima et al. | 604/385.101 |
| 2001/0016719 | A1 * | 8/2001 | Mishima | 604/385.19 |
| 2002/0010453 | A1 * | 1/2002 | Mishima et al. | 604/385.19 |
| 2002/0013567 | A1 * | 1/2002 | Mishima et al. | 604/385.101 |
| 2002/0072727 | A1 * | 6/2002 | Mishima et al. | 604/385.25 |
| 2002/0077615 | A1 * | 6/2002 | Mishima | 604/385.01 |
| 2002/0099351 | A1 * | 7/2002 | Onishi et al. | 604/385.19 |
| 2002/0111594 | A1 * | 8/2002 | Onishi et al. | 604/379 |
| 2002/0120248 | A1 * | 8/2002 | Onishi et al. | 604/385.19 |
| 2002/0151861 | A1 | 10/2002 | Klemp et al. | |
| 2002/0173763 | A1 * | 11/2002 | Tsuji et al. | 604/385.19 |
| 2003/0114819 | A1 * | 6/2003 | Sayama et al. | 604/378 |
| 2004/0122404 | A1 | 6/2004 | Meyer et al. | |
| 2004/0127864 | A1 * | 7/2004 | Sugito | 604/346 |
| 2005/0228357 | A1 * | 10/2005 | Mishima et al. | 604/385.19 |
| 2005/0228358 | A1 * | 10/2005 | Mishima et al. | 604/385.19 |
| 2006/0009746 | A1 * | 1/2006 | Nakajima et al. | 604/385.19 |
| 2006/0135931 | A1 * | 6/2006 | Suzuki et al. | 604/385.19 |
| 2007/0106240 | A1 * | 5/2007 | Nakajima et al. | 604/385.19 |

FOREIGN PATENT DOCUMENTS

| | | |
|---|---|---|
| EP | 1 064 899 A1 | 1/2001 |
| JP | 05-285174 A | 11/1993 |
| JP | 11-318976 | 11/1999 |
| JP | 11-342156 A | 12/1999 |
| JP | 2000-126227 A | 5/2000 |
| WO | 94/14395 A1 | 7/1994 |
| WO | 00/28929 A1 | 5/2000 |

* cited by examiner

DISPOSABLE WEARING ARTICLE HAVING A TRANSVERSE PARTITION

RELATED APPLICATIONS

The present application is based on, and claims priority from, Japanese Application Number 2004-160757, filed May 31, 2004, the disclosure of which is hereby incorporated by reference herein in its entirety.

BACKGROUND OF THE INVENTION

The present invention relates to disposable wearing articles adapted for absorption and containment of bodily waste such as disposable diapers.

There have already been proposed disposable wearing articles configured by front and rear ends extending in a transverse direction and side edges extending in a longitudinal direction so that front and rear waist regions extending between said front and rear ends with interposition of a crotch region. The wearing article comprises a body-faceable liquid-pervious topsheet, a garment feceable liquid-impervious backsheet, a pair of leak-barrier sheets extending in the longitudinal direction above the topsheet and a liquid-absorbent core interposed between the top- and backsheets so as to extend between the front and rear waist regions. The core is formed with a plurality of raised ridges, each extending in the transverse direction, spaced apart one from another by a predetermined dimension in the longitudinal direction and a partition sheet extends upward from the upper surface of the topsheet. One of such articles are disclosed in Japanese Unexamined Patent Application Publication No. 1999-318976, hereinafter referred to as "Reference".

In Reference, the raised ridges are formed on a rear half of the crotch region divided by a transverse centerline bisecting a longitudinal dimension of the article and in the rear waist region. The partition sheet is disposed in a vicinity of the transverse centerline. It is claimed that loose passage discharged onto the article in the rear half of the crotch region and in the rear waist region is prevented by the raised ridges and the partition sheet from flowing forward into a front half of the crotch region and further flowing forward into the front waist region whereby the article wearer's genital organ is protected from being contaminated with loose passage.

However, the article disclosed in Reference has a problem such that the sheet member may readily collapse as the wearer's body weight is exerted on the crotch region which is thereby compressed into the wearer's crotch region transversely inward. The sheet member having collapsed in this manner can no more function as a barrier adapted to prevent loose passage from further flowing beyond this barrier and consequentially loose passage may flow beyond this sheet member into the front half of the crotch region and even into the front waist region. In the case of this wearing article, the wearer's genital organ is always in contact with the outer surface of the topsheet during use of the article, so the wearer's genital organ may be soiled with loose passage spreading over the outer surface of the topsheet if loose passage flows into the front half of the crotch region and further into the front waist region.

SUMMARY OF THE INVENTION

In view of the problem as has been described above, it is an object of the present invention to provide a disposable wearing article improved so that the wearer's genital organ can be reliably protected from being soiled with loose passage even if the loose passage moves toward a front half of the crotch region and the front waist region.

According to a first aspect of the present invention, there is provided a disposable wearing article comprising: a front waist region; a rear waist region; a crotch region; a body-faceable liquid-pervious topsheet; an opposed liquid-impervious backsheet; and a liquid-absorbent core interposed between the top- and backsheets so as to extend between the front and rear waist regions.

The article according to the present invention further comprises a partition extending in a longitudinal direction of the article above the topsheet is laid in the front waist region plus a front half of the crotch region divided by a transverse centerline bisecting a longitudinal dimension of the article or at least in the front half of the crotch region, and the partition having transversely opposite side edges bonded to opposite side edges of the article and an intermediate zone defined between the side edges left free from the article.

According to a second aspect of the present invention, there is provided a disposable wearing article comprising: a front waist region; a rear waist region; a crotch region; a body-faceable liquid-pervious topsheet; an opposed liquid-impervious backsheet; a liquid-absorbent core interposed between the top- and backsheets so as to extend between the front and rear waist region; a pair of leak-barrier flaps extending in a longitudinal direction of the article above the topsheet; wherein the leak-barrier flaps have proximal zones bonded to opposite side edges of the article so as to extend in the longitudinal direction, distal zones extending in the longitudinal direction and normally biased to rise up above the topsheet, longitudinally opposite end zones collapsed in a transverse direction of the article bonded in such collapsed state to longitudinally opposite ends of the article and stretch- and contractable elastic members extending in the longitudinal direction and bonded in a stretch state to the distal zones of the leak-barrier flaps.

The article according to the second aspect of the present invention further comprises a partition which extends between the leak-barrier flaps in the transverse direction above the topsheet being laid in the front waist region and a front half of the crotch region divided by a transverse centerline bisecting a longitudinal dimension of the article or at least in the front half of the crotch region, and the partition having transversely opposite side edges bonded to the respective distal zones of the leak-barrier flaps and intermediate portion defined between the side edges and left free from the article.

The present invention in the first aspect may include the following preferable embodiments.

(1) The article further comprises a pair of leak-barrier flaps extending in the longitudinal direction above the topsheet, these leak-barrier flaps having lateral zones bonded to side edges of topsheet so as to extend in the longitudinal direction, distal zones extending in the longitudinal direction and normally biased to rise up above said topsheet, and front and rear ends collapsed in a transverse direction of the article and bonded in such collapsed state to the front and rear ends of the article wherein the leak-barrier flaps are provided with stretch- and contractable elastic members attached in a stretched state to the distal zones, and the partition being laid between the leak-barrier flaps and, at least in a vicinity of the transverse centerline, having transversely opposite regions of the intermediate zone bonded to the respective distal zones of the leak-barrier flaps so that the intermediate zone is lifted above the topsheet as the respective distal zones of the leak-barrier flaps rise up above the topsheet.

(2) There is further provided a spacer which is elastically stretch- and contractable and extends in the transverse direction, the spacer having side edges bonded to the respective side edges of the partition and a middle zone extending between the lateral zones and left free from the partition so that the lateral zones of the partition are drawn toward each other in the transverse direction of the article under a contractile force of the spacer and the intermediate zone of the partition curves in the transverse direction so as to describe a generally circular arc which is convex upward above the topsheet.

The present invention in the first and second aspects may include the following preferred embodiments.

(3) The partition is formed from at least one water-absorbent sheet.

(4) The partition is formed from at least one water-absorbent sheet and absorbent core material wrapped with the water-absorbent sheet and wherein the absorbent core material is at least one of a mixture of super-absorbent polymers and fluff pulp fibers and a foam material.

(5) The partition is formed from at least one body-faceable water-absorbent sheet, an opposed liquid-impervious sheet and an absorbent core material interposed between the water-absorbent sheet and the liquid-impervious sheet and wherein the absorbent core material is at least one of a mixture of super-absorbent polymers and fluff pulp fibers and a foam material.

With the disposable wearing article according to the present invention being worn, a dimension by which the transversely opposite lateral zones of the partition is reduced and the intermediate zone of the partition is spaced upward from the topsheet in an upward convex circular arc-shape extending in the transverse direction as the crotch region of the article is squeezed between the wearer's thighs inward as viewed in the transverse direction of the article. It is ensured thereby that the genital organ of the wearer is reliably spaced from the outer surface of the topsheet. During use of the article, the wearer's genital organ is held in contact with the outer surface of the partition describing a generally circular art which is convex upward above the topsheet. In this way, there is no anxiety that the genital organ might be soiled with loose passage even if loose passage spreads on the topsheet.

In the case of the article wherein the intermediate zone of the partition has its transversely opposite lateral portions bonded to the distal zones of the leak-barrier flaps at least in the region placed aside toward the transverse centerline, the intermediate zone of the partition is raised up from the topsheet as the distal zones of the leak-barrier flaps are raised up so that the intermediate zone is spaced upward from the topsheet. In this article also, a dimension by which the transversely opposite lateral zones of the partition is reduced and the intermediate zone of the partition is spaced upward from the topsheet in an upward convex circular arc-shape extending in the transverse direction as the crotch region of the article is squeezed between the wearer's thighs inward as viewed in the transverse direction of the article. In this way, it is ensured that the wearer's genital organ normally placed against the outer surface of the partition is reliably spaced from the topsheet and reliably protected from soiling with loose passage.

In the case of the article including an elastically stretchable spacer extending in the transverse direction is attached in a stretched state between the topsheet and the partition, the transversely opposite lateral zones of the partition are drawn toward each other in the transverse direction of the article under a contractile force of the spacer and the intermediate zone of the partition curves in the transverse direction so as to describe a generally circular arc which is convex upward above the topsheet. In this article also, a dimension by which the transversely opposite lateral zones of the partition is reduced and the intermediate zone of the partition is spaced upward from the topsheet in an upward convex circular arc-shape extending in the transverse direction as the crotch region of the article is squeezed between the wearer's thighs inward as viewed in the transverse direction of the article. In this way, it is ensured that the wearer's genital organ normally placed against the outer surface of the partition is reliably spaced from the topsheet and reliably protected from soiling with loose passage.

In the case of the article wherein the transversely opposite lateral zones of the partition are bonded to the distal zones of the respective leak-barrier flaps, the lateral zones as well as the intermediate zone of the partition are raised up above the topsheet as the distal zones of the respective leak-barrier flaps rise up above the topsheet. In this article also, a dimension by which the transversely opposite lateral zones of the partition is reduced and the intermediate zone of the partition is spaced upward from the topsheet in an upward convex circular arc-shape extending in the transverse direction as the crotch region of the article is squeezed between the wearer's thighs inward as viewed in the transverse direction of the article. In this way, it is ensured that the wearer's genital organ normally placed against the outer surface of the partition is reliably spaced from the topsheet and reliably protected from soiling with loose passage.

In the case of the article having the partition formed from at least one water-absorbent sheet, such water-absorbent sheet can absorb urine discharged onto the article and thereby prevent feces from commingling with urine. In this way, it can be avoided that feces might be fluidized and the wearer's skin might be contaminated with such fluidized feces.

In the case of the article having the partition formed from a water-absorbent sheet and an absorbent core material wrapped with the water-absorbent sheet, urine discharged onto the partition is absorbed through the water-absorbent sheet by the absorbent core material and contained therein. In this way, a large amount of urine can be absorbed by the partition. With this article also, it can be avoided that feces might commingle with urine to be fluidized and the wearer's skin might be soiled with such fluidized feces.

In the case of the article having the partition formed from the water-absorbent sheet, a liquid-impervious sheet and an absorbent core interposed between these sheets, urine discharged onto the partition is absorbed through the water-absorbent sheet by the absorbent core and contained therein so that a large amount of urine may be absorbed by the partition. With this article, it is unlikely that the amount of urine once having been absorbed by the partition might permeate the liquid-impervious sheet and reach the topsheet. In this way, a large amount of urine can be absorbed by the partition. With this article also, it can be avoided that feces might commingle with urine to be fluidized and the wearer's skin might be soiled with such fluidized feces.

DETAILED DESCRIPTION OF THE PREFERRED EMBODIMENTS

Details of a disposable wearing article according to the present invention will be more fully understood from the description given hereunder with reference to the accompanying drawings.

Figure 1:
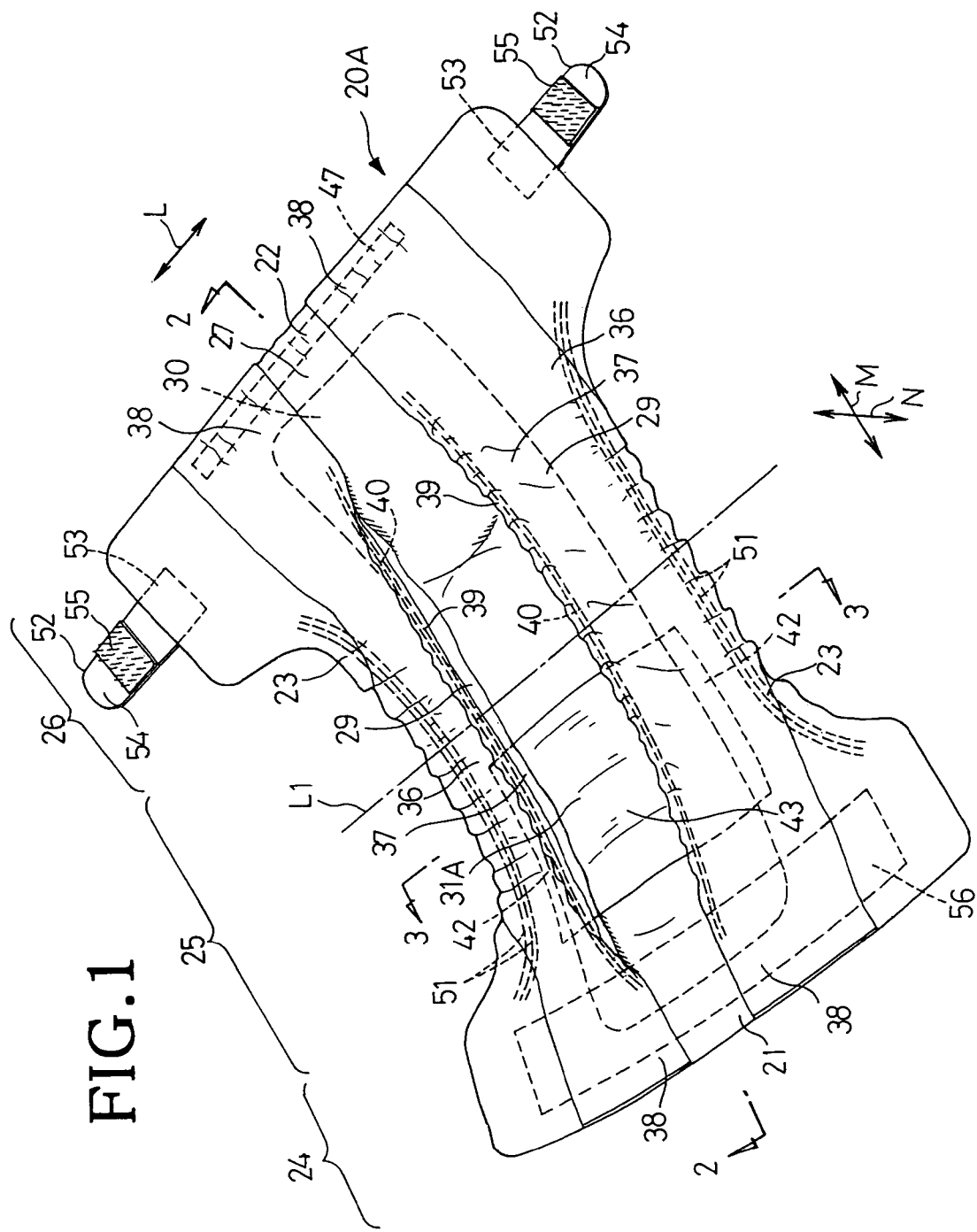
FIG. 1 is a partially cutaway perspective view showing a typical embodiment of a disposable wearing article according to the invention.
Figure 2:
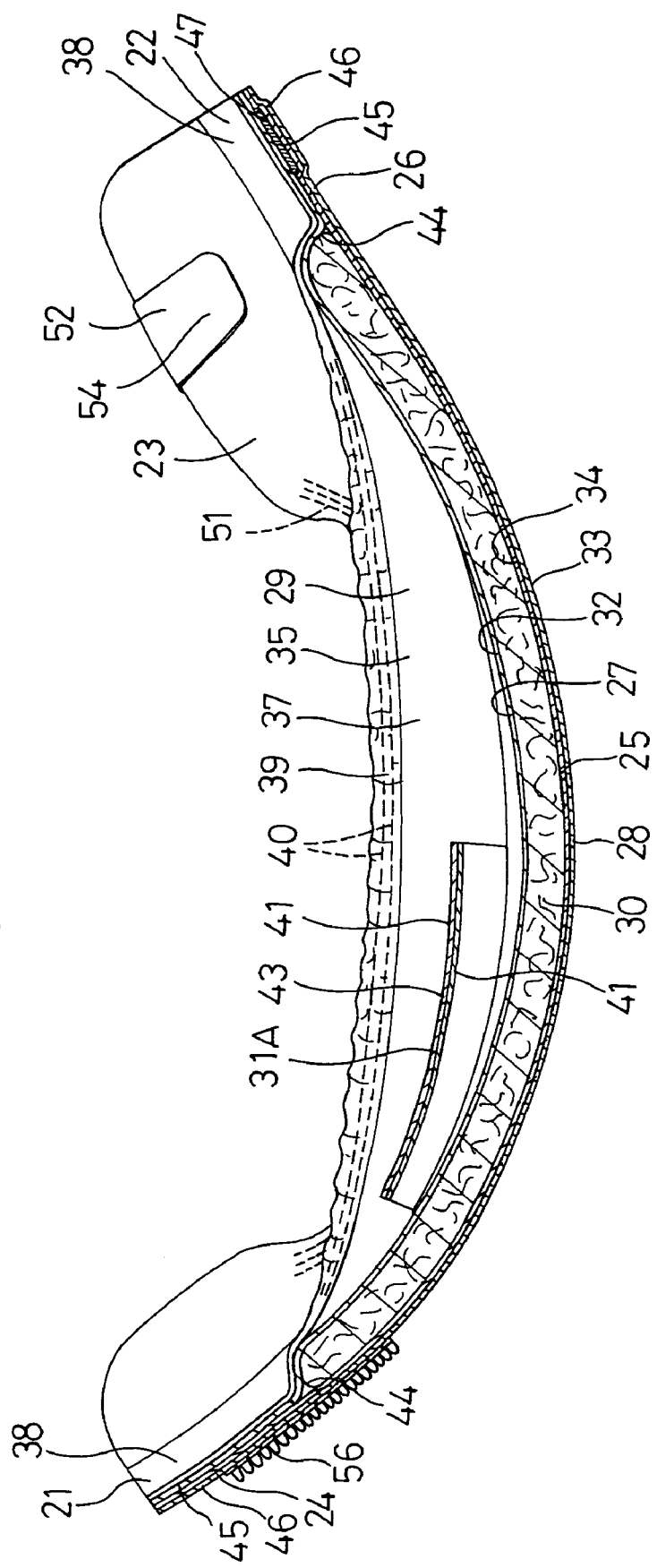
FIG. 2 is a sectional view taken along the line 2-2 in FIG. 1.
Figure 3:
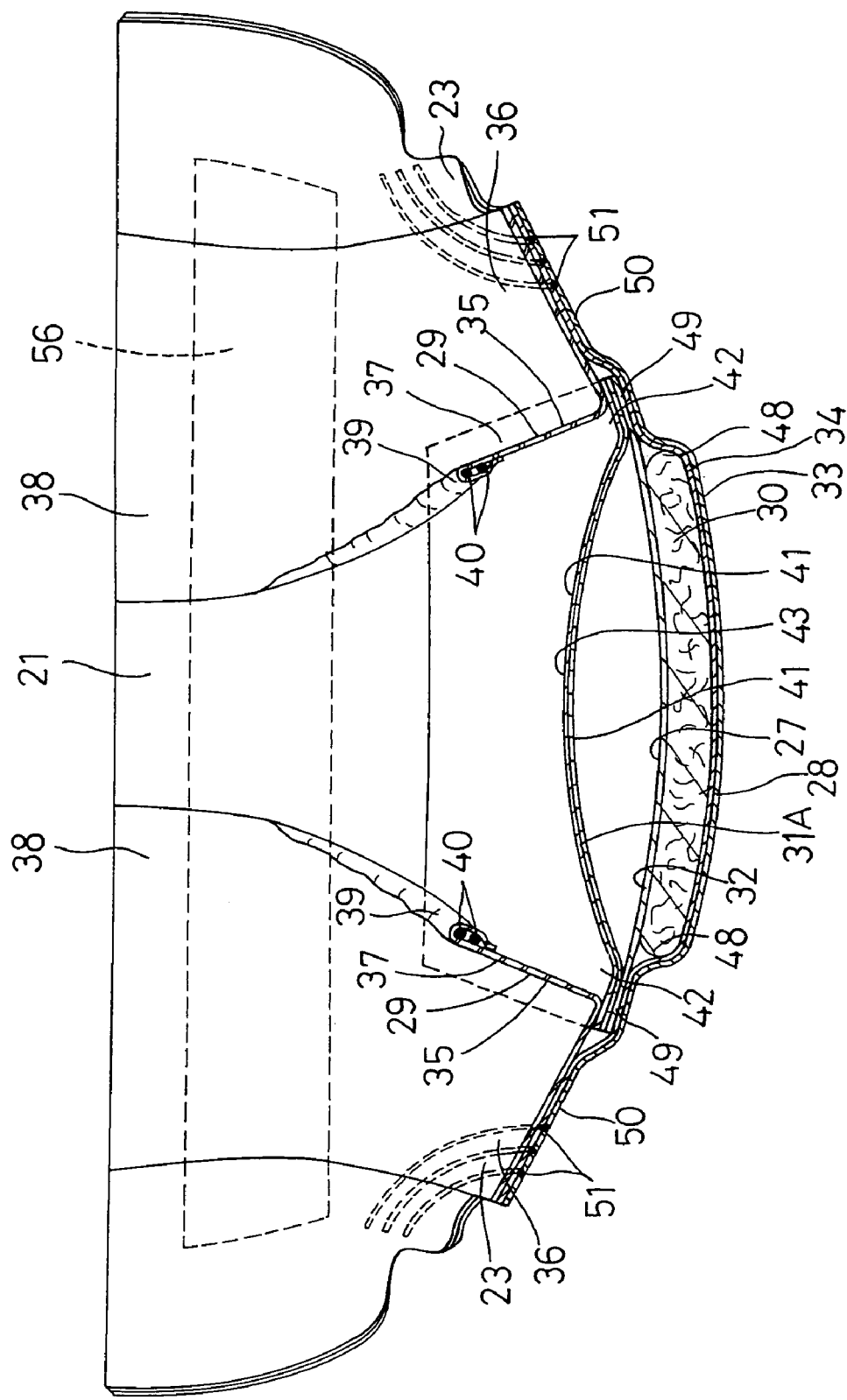
FIG. 3 is a sectional view taken along the line 3-3 in FIG. 1.

FIG. 1 is a perspective view showing a disposable wearing article 20A as a typical embodiment of the invention, FIG. 2 is a sectional view taken along the line 2-2 in FIG. 1 and FIG. 3 is a sectional view taken along the line 3-3 in FIG. 1. In FIG. 1, a transverse direction is indicated by an arrow L, a longitudinal direction is indicated by an arrow M and a thickness direction is indicated by an arrow N. As used herein the term "inner surfaces" of top- and backsheets 27, 28, leak-barrier flaps 29 and a partition 31A refer to the respective surfaces thereof faceable a core 30 and the term "outer surfaces" thereof refer to the respective surfaces thereof facing away from the core 30.

The article 20A is configured by front and rear ends 21, 22 extending in parallel to each other in the transverse direction, side edges 23 extending in the longitudinal direction so as to define front and rear waist regions 24, 26 extending in the longitudinal direction between the front and rear ends 21, 22 with interposition of a crotch region 25. The wearing article 20A comprises a body-faceable liquid-pervious topsheet 27, a garment-faceable liquid-impervious backsheet 28, a pair of liquid-impervious leak-barrier flaps 29 lying on the side of outer surface of the topsheet 27 and extending in the longitudinal direction and a liquid-absorbent core 30 interposed between the top- and backsheets 27, 28 and bonded to the inner surfaces of these sheets 27, 28. The core 30 is placed so as to occupy the front and rear waist regions 24, 26 as well as the crotch region 25 except the front and rear ends 21, 22 and the side edges 23. In the crotch region 25, the side edges 23 respectively describe generally circular arcs which are convex transversely inward of the article 20A. Thus, the article 20A has a generally hourglass-like planar shape. Between the leak-barrier flaps 29, there is provided a body-faceable partition 31A extending lying above the topsheet 27 and extending in the transverse direction.

The topsheet 27 is formed from a hydrophilic fibrous nonwoven fabric 32. The backsheet 28 is formed from a composite sheet composed of a hydrophobic fibrous nonwoven fabric layer 33 and a breathable liquid-impervious plastic film layer 34 laminated together. Each of the leak-barrier flaps 29 is formed from a repellent treated hydrophobic nonwoven fabric 35. The core 30 comprises a mixture of particulate or fibrous super-absorbent polymers and fluff pulp fibers or a mixture of particulate or fibrous super-absorbent polymers, fluff pulp fibers and thermoplastic synthetic resin fibers, in any case, compressed to a given thickness. The core 30 has a stiffness higher than those of the top- and backsheets 27, 28 and the leak-barrier flaps 29. The core 30 is entirely wrapped with a liquid-absorption and diffusion sheet such as a tissue paper or hydrophilic fibrous nonwoven fabric or the like (not shown) in order to prevent the core 30 from getting out of its initial shape.

The leak-barrier flaps 29 extend between the front and rear ends 21, 22 of the article 20A. Each of the leak-barrier flaps 29 has a proximal zone 36 bonded to the associated one of the side edges 23 and extending in the longitudinal direction, a distal zone 37 extending in the longitudinal direction in parallel to the proximal zone 36 and normally biased to rise up above the topsheet 27 and front and rear ends 38 collapsed inward in the transverse direction of the article 20A and bonded in such a collapsed state to the front and rear ends 21, 22.

A stretch- and contractable elastic member 40 extending in the longitudinal direction is secured to the distal zone 37 in the vicinity of its distal edge 39 while the elastic member 40 is stretched at a predetermined ratio in the longitudinal direction. Contraction of the elastic member 40 causes the article 20A to curve along the longitudinal direction with the topsheet 27 inside and at the same time causes the distal zone 37 of the leak-barrier flaps 29 to contract in the longitudinal direction so that the distal zone 37 of the leak-barrier flaps 29 rises up above the topsheet 27 and form a barrier against bodily waste. The distal zone 37 of the leak-barrier flap 29 rising up in this manner reliably prevents bodily waste from leaking sideways out from the article 20A.

The partition 31A has a rectangular shape which is relatively long in the transverse direction and is laid on a front half of the crotch region 25 divided by a transverse centerline L1 bisecting a longitudinal dimension of the article 20A. The partition 31A comprises a pair of hydrophilic nonwoven fabric layers 41 (which may be referred to as "water-absorbent sheets") laminated together. These nonwoven fabric layers 41 have respective surfaces opposed to each other intermittently and bonded together by means of adhesives (not shown). The partition 31A has transversely opposite side edges 42 bonded to the respective side edges 23 of the article 20A and an intermediate zone 43 extending between the side edges 42 and left free from the article 20A.

The front and rear ends 21, 22 of the article 20A are respectively formed from longitudinally opposite ends 45, 46 of the top- and backsheets 27, 28 extending outward beyond longitudinally opposite ends 44 of the core 30 and the longitudinally opposite ends 38 of the leak-barrier flaps 29. Along the longitudinally opposite ends 21, 22, the ends 45, 46 of the top- and backsheets 27, 28 are placed upon the ends 38 of the leak-barrier flaps 29, the respective inner surfaces of the top- and backsheets 27, 28 are bonded one to another and the topsheet 27 is bonded to the respective inner surfaces of the leak-barrier flaps 29. A ribbon-like waist-surrounding elastic member 47 extending in the transverse direction is secured in a stretched state to the rear end 22. This waist-surrounding elastic member 47 is interposed between the end 45 of the topsheet 27 and the end 46 of the backsheet 28 and bonded to the respective inner surfaces of these sheets 27, 28 while stretched at a predetermined ratio in the transverse direction.

The transversely opposite side edges 23 of the article 20A are respectively formed from transversely opposite side edges 49, 50 of the top- and backsheets 27, 28 and the proximal zones 36 of the leak-barrier flaps 29. Along the transversely opposite side edges 23, the side edges 49 of the topsheet 27 extend outward slightly beyond transversely opposite side edges 48 of the core 30, the side edges 50 of the backsheet 28 and the respective proximal zones 36 of the leak-barrier flaps 29 extend further outward beyond the side edges 49. Along the side edges 23, the side edges 49, 50 of the top- and backsheets 27, 28 and the proximal zones 36 of the leak-barrier flaps 29 are placed one upon another, the respective inner surfaces of the top- and backsheets 27, 28 are bonded together, and the mutually opposing surfaces of the top- and backsheets 27, 28 and the respective inner surfaces of the leak-barrier flaps 29 are bonded together. The side edges 42 of the partition 31A are interposed between the side edges 49 of the topsheet 27 and the proximal zones 36 of the leak-barrier flaps 29 and bonded to the mutually opposing surfaces of these sheets 27, 29. A plurality of leg-surrounding elastic members 51 extending along the side edges 23 of the crotch region 25 are secured in a stretched state. Leg-surrounding elastic members 51 are interposed between the nonwoven fabric layer 33 and the film layer 34 constituting the backsheet 28 and secured to the mutually opposed surfaces of these nonwoven fabric layers while stretched at a predetermined ratio in its longitudinal direction.

Tape fasteners 52 made of a plastic film are respectively attached to the side edges 23 of the rear waist region 26. These tape fasteners 52 respectively have fixed end segments 53 and free end segments 54 both extending in the transverse direction. The fixed end segments 53 are interposed between the nonwoven fabric 33 and the film 34 and bonded to the mutually opposing surfaces thereof. Male mechanical fasteners 55 having a plurality of hook elements are attached to the inner surfaces of the respective free end segments 54. The respective free end segments 54 are folded inward as viewed in the transverse direction of the article 20A and releasably engaged with the respective outer surfaces of the proximal zones 36 of the leak-barrier flaps 29 by means of the hook elements (See FIG. 2). It should be understood that the mechanical fasteners 55 provided on the respective free end segments 54 may be replaced by a pressure-sensitive adhesive coated on these free end segments 54.

The front waist region 24 is provided with a target tape strip 56 on which the free end segments 54 of the respective tape fasteners 52 are destined to be detachably anchored. The target tape strip 56 is formed from a plastic film strip and a female mechanical fastener comprising a plurality of loop elements. The target tape strip 56 has a rectangular shape which is relatively long in the transverse direction and bonded to the outer surface of the backsheet 28, i.e., the nonwoven fabric 33. When it is desired to coat the free end segments 54 of the respective tape fasteners 52 with a pressure-sensitive adhesive, a plastic film is used as a stock material for the target tape strip 56.

Figure 4:
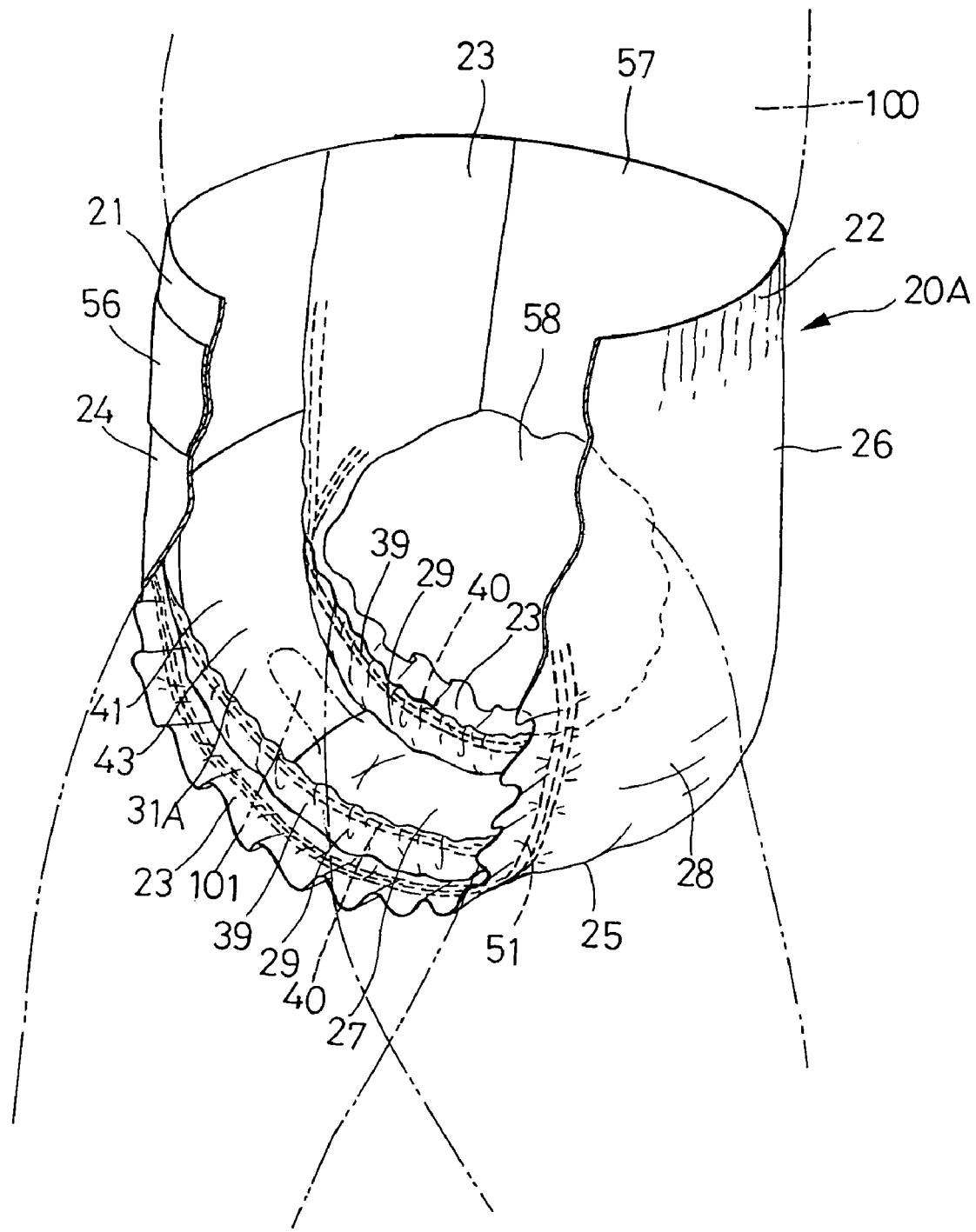
FIG. 4 is a perspective view showing the article of FIG. 1 as put on a wearer's body.

FIG. 4 is a perspective view showing the article 20A of FIG. 1 as put on the wearer's body, in which the front and rear waist regions 24, 26 are illustrated with one of the side edges 23 cut away. To wear the article 20A, the side edges 23 of the rear waist region 26 are placed on the side edges 23 of the front waist region 24 from the outside, then the free end segments 54 of the respective tape fasteners 52 are pressed against the target tape strip 56 to bring the hook elements in engagement with the loop elements and thereby the free end segments 54 are anchored on the target tape strip 56. Thus the front and rear waist regions 24, 26 are connected with each other and thereupon the article 20A is formed with a waist-hole 57 and a pair of leg-holes 58.

During use of the wearing article 20A, the buttock of the wearer 100 is in contact with the outer surface of the topsheet 27 and the penis 101 (genital organ) of the wearer 100 is in contact with the outer surface of the intermediate zone 43 of the partition 31A. The crotch region 25 of the article 20A is normally squeezed between the thighs of the wearer 100 inward as viewed in the transverse direction and thereby the distance between the side edge zones 42 of the partition 31A is reduced. Consequentially, the intermediate zone 43 rises up above the topsheet 27 so as to describe an upward convex circular arc extending in the transverse direction and to be spaced upward from the topsheet 27. Urine discharged is absorbed by the partition 31A while loose passage discharged is absorbed by the core 30 through the topsheet 27 and contained therein.

During use of the article 20A, the penis 101 of the wearer 100 comes in contact with the partition 31A but not in contact with the topsheet 27. Even if loose passage discharged onto the rear half of the crotch region 25 as well as onto the rear waist region 26 spreads on the topsheet 27 and move to the front half and the front waist region 24, the partition 31A interposed between the topsheet 27 and the penis 101 prevents such loose passage from clinging to and soiling the penis 101.

During use of the article 20A, the intermediate zone 43 of the partition 31A curves in the transverse direction so as to be spaced upward from the topsheet 27, so any amount of loose passage can not transfer from the topsheet 27 to the partition 31A. In addition, the penis 101 is spaced upward from the topsheet 27 as the intermediate zone 43 is spaced from the topsheet 27. Consequently, the penis 101 can be reliably protected from soiling with loose passage. The article 20A ensures that urine discharged is absorbed by the partition 31A adequately to prevent such urine from being mixed with feces and thereby to prevent feces from being further fluidized. In this way, the skin of the wearer is reliably protected from soiling with such excessively fluidized feces.

Figure 5:
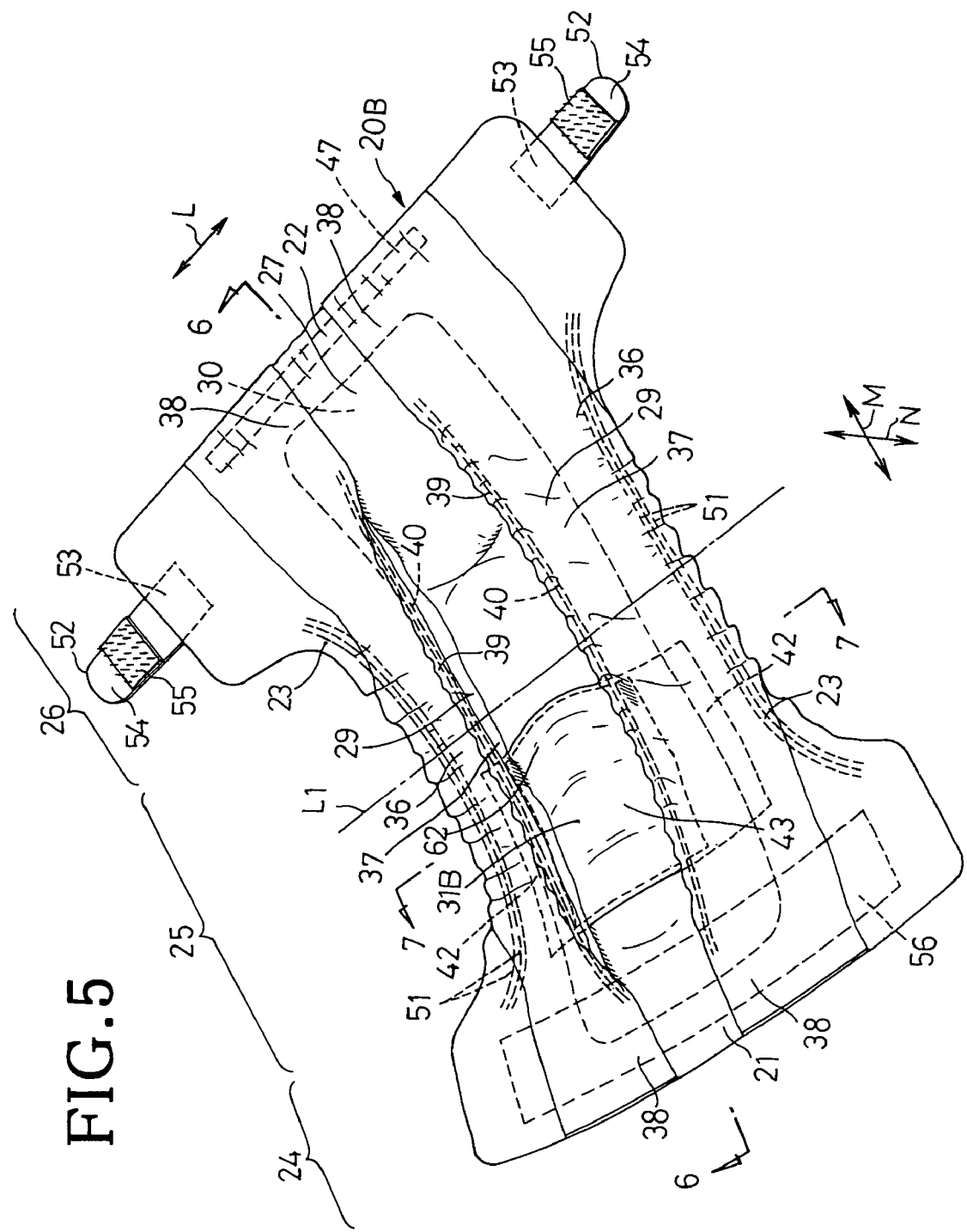
FIG. 5 is a partially cutaway perspective view showing one preferred embodiment of the disposable wearing article according to the invention.
Figure 6:
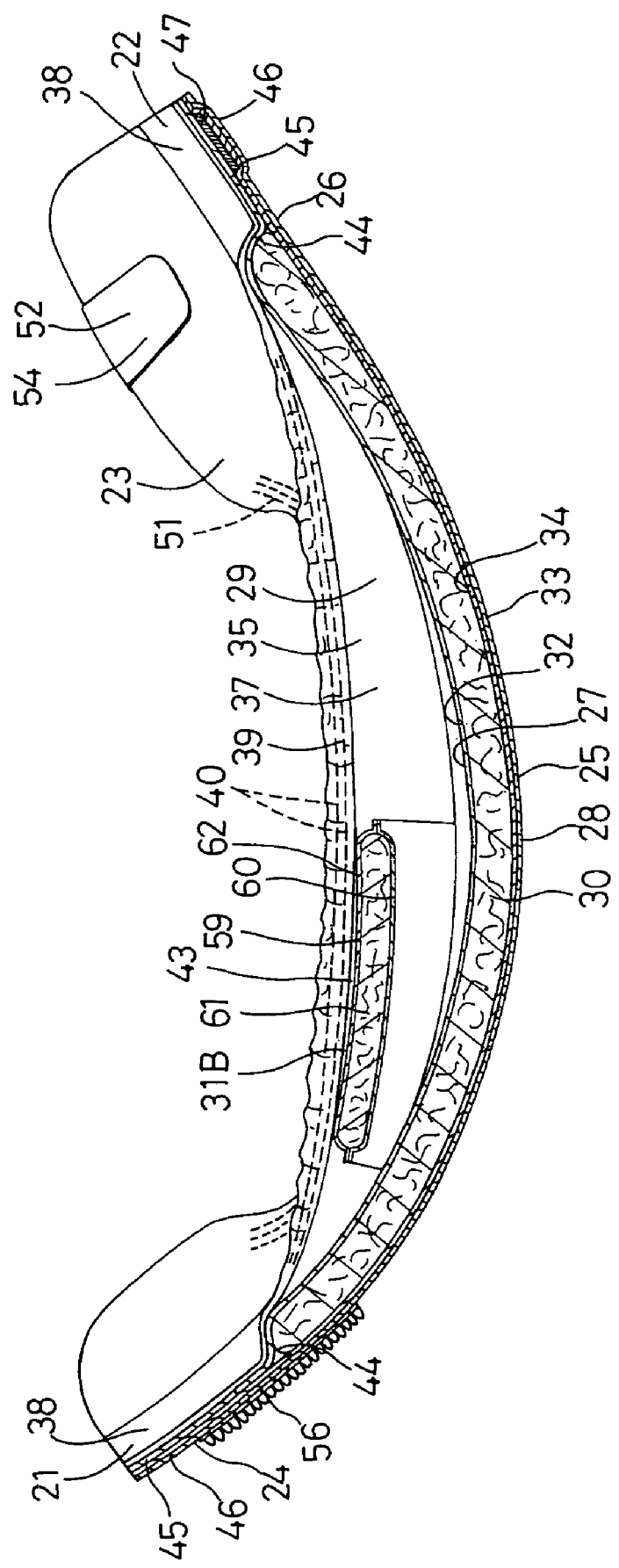
FIG. 6 is a sectional view taken along the line 6-6 in FIG. 5.
Figure 7:
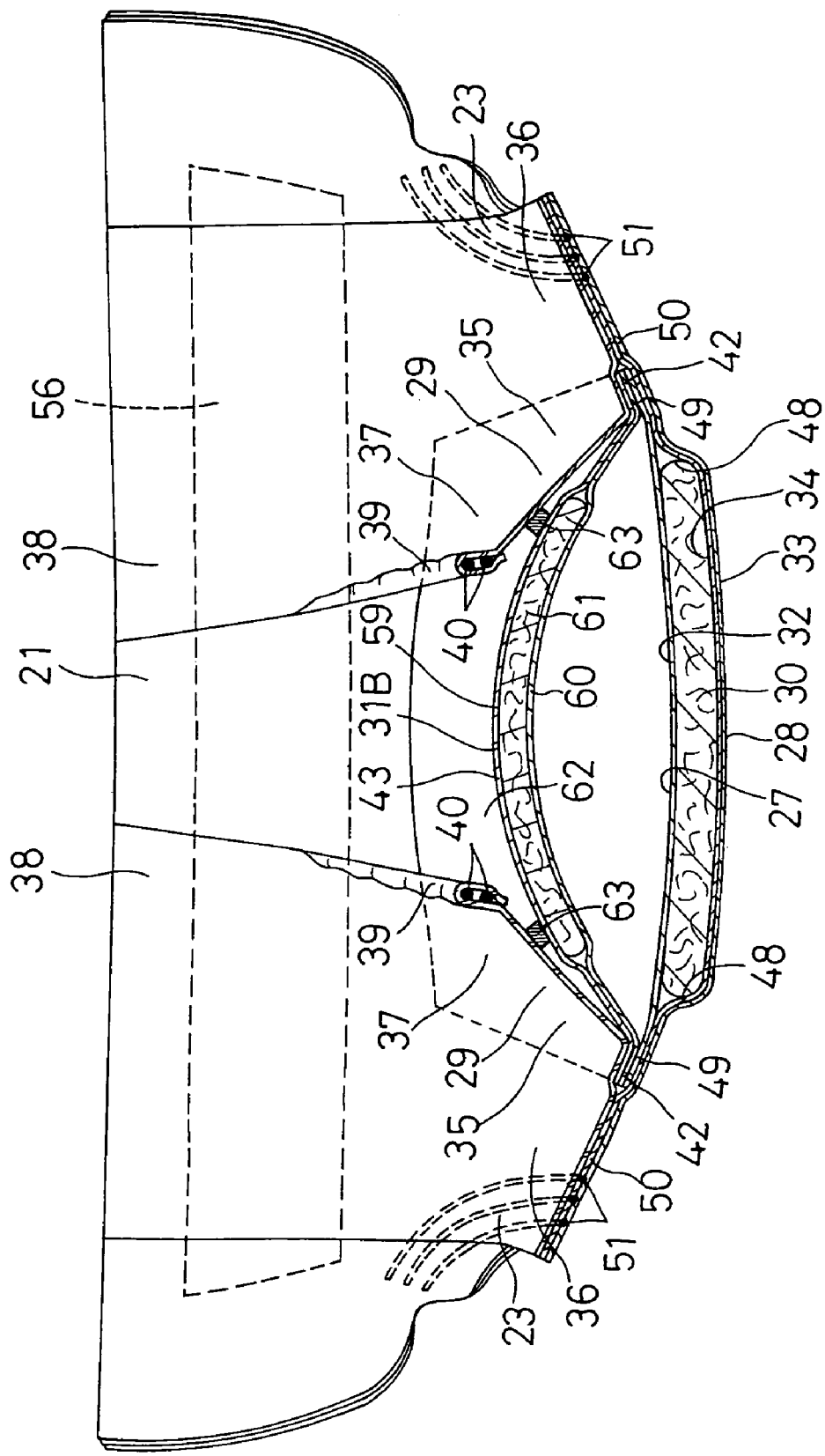
FIG. 7 is a sectional view taken along the line 7-7 in FIG. 5.

FIG. 5 is a perspective view showing a disposable article 20B as one preferred embodiment of the invention, FIG. 6 is a sectional view taken along the line 6-6 in FIG. 5 and FIG. 7 is a sectional view taken along the line 7-7 in FIG. 5. In FIG. 5, a transverse direction is indicated by an arrow L, a longitudinal direction is indicated by an arrow M and a thickness direction is indicated by an arrow N. As used herein the term "inner surfaces" of first and second fibrous nonwoven fabrics 59, 60 refer to the respective surfaces thereof facing a core 61 and the term "outer surfaces" thereof refer to the respective surfaces thereof facing away from the core 61.

The article 20B is similar to the article 20A except that the article 20B includes a partition 31B in place of the partition 31A. The components similar to those in FIGS. 1-4 are denoted by the same reference numerals and the description of the arrangements similar to those in FIGS. 1-4 will be omitted here.

The partition 31B is of a rectangular shape which is relatively long in the transverse direction and laid in a front half of the crotch region 25 divided by the transverse centerline L1. The partition 31B comprises a body-faceable first hydrophilic nonwoven fabric layer 59 (which may be referred to as "water-absorbent sheet"), an opposed second hydrophilic fibrous nonwoven fabric layer 60 (which may be referred to as "water-absorbent sheet") and a liquid-absorbent core 61 (which may be referred to as "absorbent core material") interposed between the first and second fibrous nonwoven fabric layers 59, 60. These nonwoven fabric layers 59, 60 have respective portions extending outward beyond a peripheral edge of the core 61 placed upon and bonded to each other. The core 61 is intermittently bonded to the mutually opposing surfaces of these nonwoven fabrics 59, 60 by means of adhesives (not shown). The core 61 comprises the same mixture as that in the case of the core 30 entirely wrapped with a liquid-absorption and diffusion sheet such as a tissue paper, hydrophilic nonwoven fabric or the like (not shown). The core 61 has a stiffness higher than those of the first and second fibrous nonwoven fabric layers 59, 60.

The partition 31B has transversely opposite lateral zones 42 bonded to the side edges 23 of the article 20B and an intermediate zone 43 extending between the lateral zones 42 and left free from the article 20B. The lateral zones 42 are formed from the first and second fibrous nonwoven fabric layers 59, 60 except the core 61. The lateral zones 42 are interposed between the side edges 49 of the topsheet 27 and the proximal zones 36 of the leak-barrier flaps 29 and bonded to the mutually opposing surfaces of them 27, 29. The intermediate zone 43 has a region 62 placed aside toward the transverse centerline L1 and bonded at both sides of this region 62 to the distal zones 37 of the respective leak-barrier flaps 29 in the vicinity of the elastic members 40 (more specifically, in the vicinity of the distal edges 39). The region 62 is bonded to the respective distal zones 37 by means of adhesives 63. The intermediate zone 43 is raised above the topsheet 27 and spaced upward from the topsheet 27 as the distal zones 37 of the leak-barrier flaps 29 are elastically biased to rise up. Without departing from the scope of the invention, the intermediate zone 43 may be bonded along the full length thereof to the distal zones 37 of the respective leak-barrier flaps 29 in the vicinity of the elastic members 40.

Figure 8:
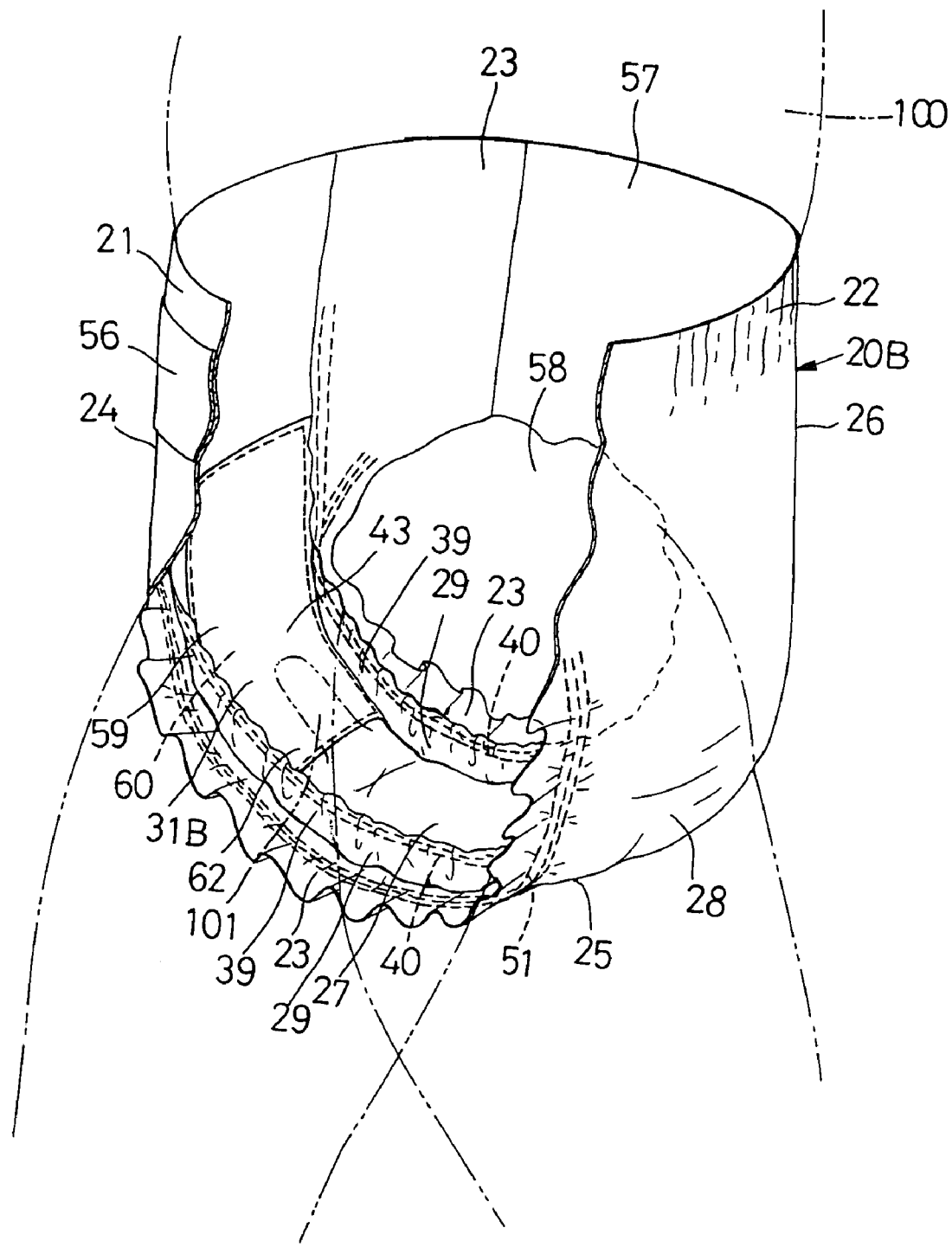
FIG. 8 is a perspective view showing the article of FIG. 5 as put on a wearer's body.

FIG. 8 is a perspective view showing the article 20B of FIG. 5 as worn, in which the side edges 23 of the front and rear waist regions 24, 26 are cut away on one side of the waist. Sequential procedures to put the article 20B on the article wearer's body are the same as in the case of the article 20A shown by FIGS. 1-4 and the description thereof is omitted here. During use of the wearing article 20B, the buttock of the wearer 100 is in contact with the topsheet 27 and the penis 101 of the wearer 100 is in contact with the outer surface of the intermediate zone 43 of the partition 31B. During use of the article 20B, the penis 101 of the wearer 100 comes in contact with the outer surface of the partition 31B but not in contact with the topsheet 27. Even if loose passage discharged onto the rear half of the crotch region 25 as well as onto the rear waist region 26 spreads on the topsheet 27 and moves toward the front half of the crotch region 25 and the front waist region 24, the partition 31B interposed between the topsheet 27 and the penis 101 prevents such loose passage from clinging to and soiling the penis 101.

During use of the article 20B, the crotch region 25 is squeezed between the thighs of the wearer 100 inward as viewed in the transverse direction and thereby the distance between the lateral zones 42 of the partition 31B is reduced. Consequentially, the intermediate zone 43 is held to curve in the transverse direction so as to describe a generally circular arc which is convex upward. In other words, the intermediate zone 43 is kept to be spaced upward from the topsheet 27. More specifically, the intermediate zone 43 of the partition 31B rises up above the distal edges 39 of the respective distal zones 37 of the leak-barrier flaps 29 as the intermediate zone 43 of the partition 31B curves in the transverse direction so as to describe the circular arc which is convex upward. Consequently, any amount of loose passage can not transfer from the topshet 27 to the partition 31B. In addition, as the intermediate zone 43 is spaced from the topsheet 27, the penis 101 can be reliably protected from soiling with loose passage. Urine discharged onto the article 20B is therefore absorbed by the core 61 through the first fibrous nonwoven fabric 59 and contained therein while feces discharged onto the article 20B is absorbed by the core 30 through the topsheet 27 and contained therein. In this way, a large amount of urine can be reliably absorbed by the partition 31B while the partition 31B can prevent such urine from being mixed with feces and thereby prevent feces from being further fluidized. Thus, the skin of the wearer is reliably protected from soiling with such excessively fluidized feces.

Figure 9:
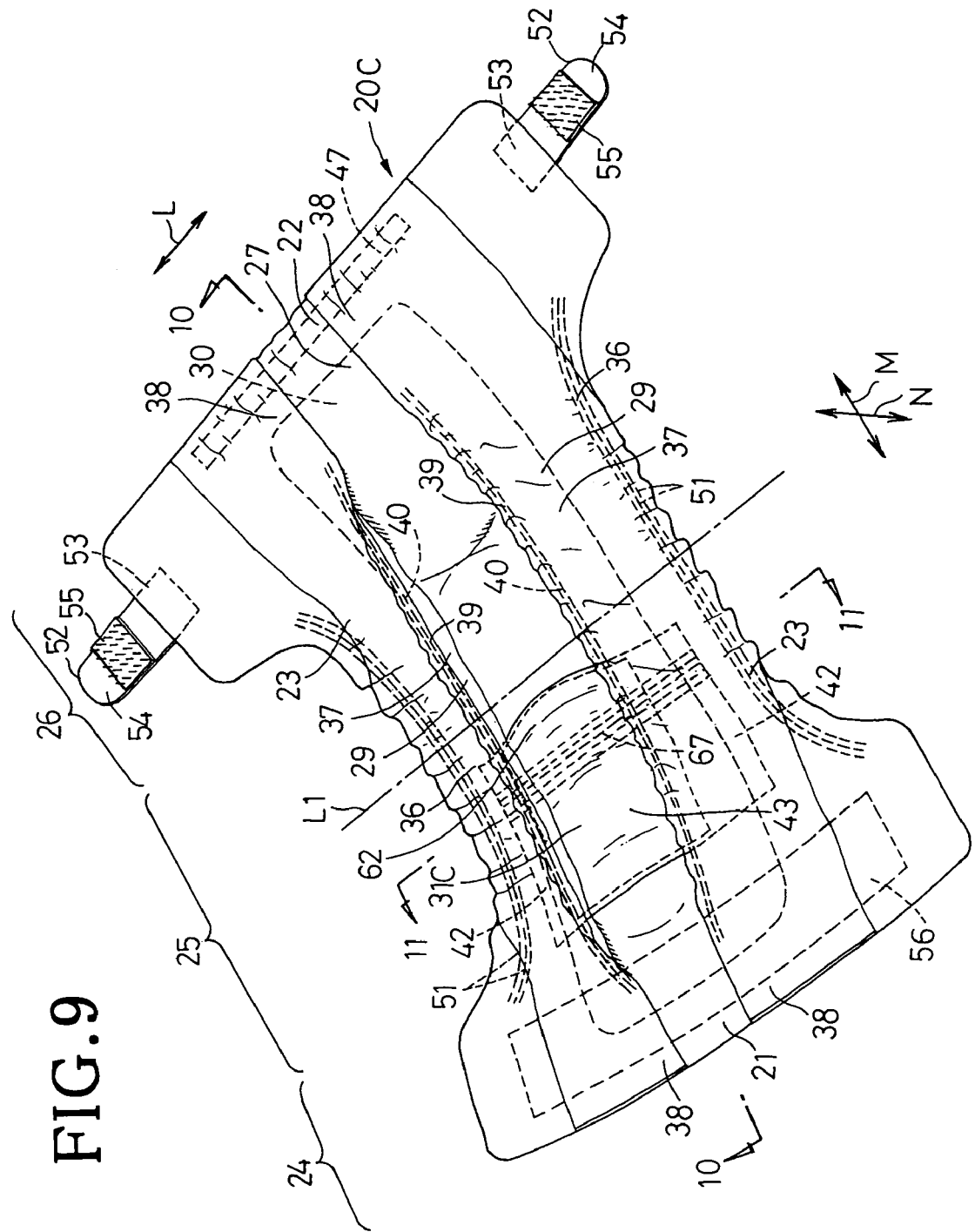
FIG. 9 is a partially cutaway perspective view showing another preferred embodiment of the disposable wearing article according to the invention.
Figure 10:
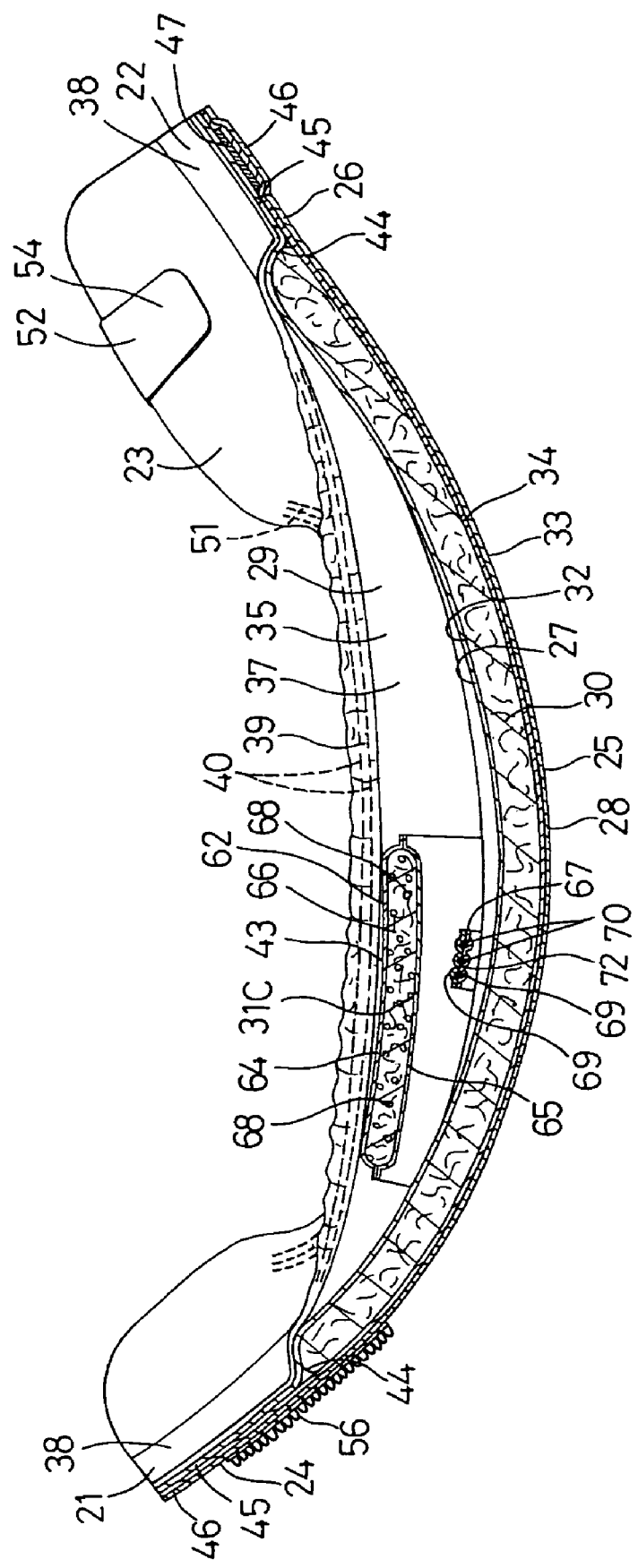
FIG. 10 is a sectional view taken along the line 10-10 in FIG. 9.
Figure 11:
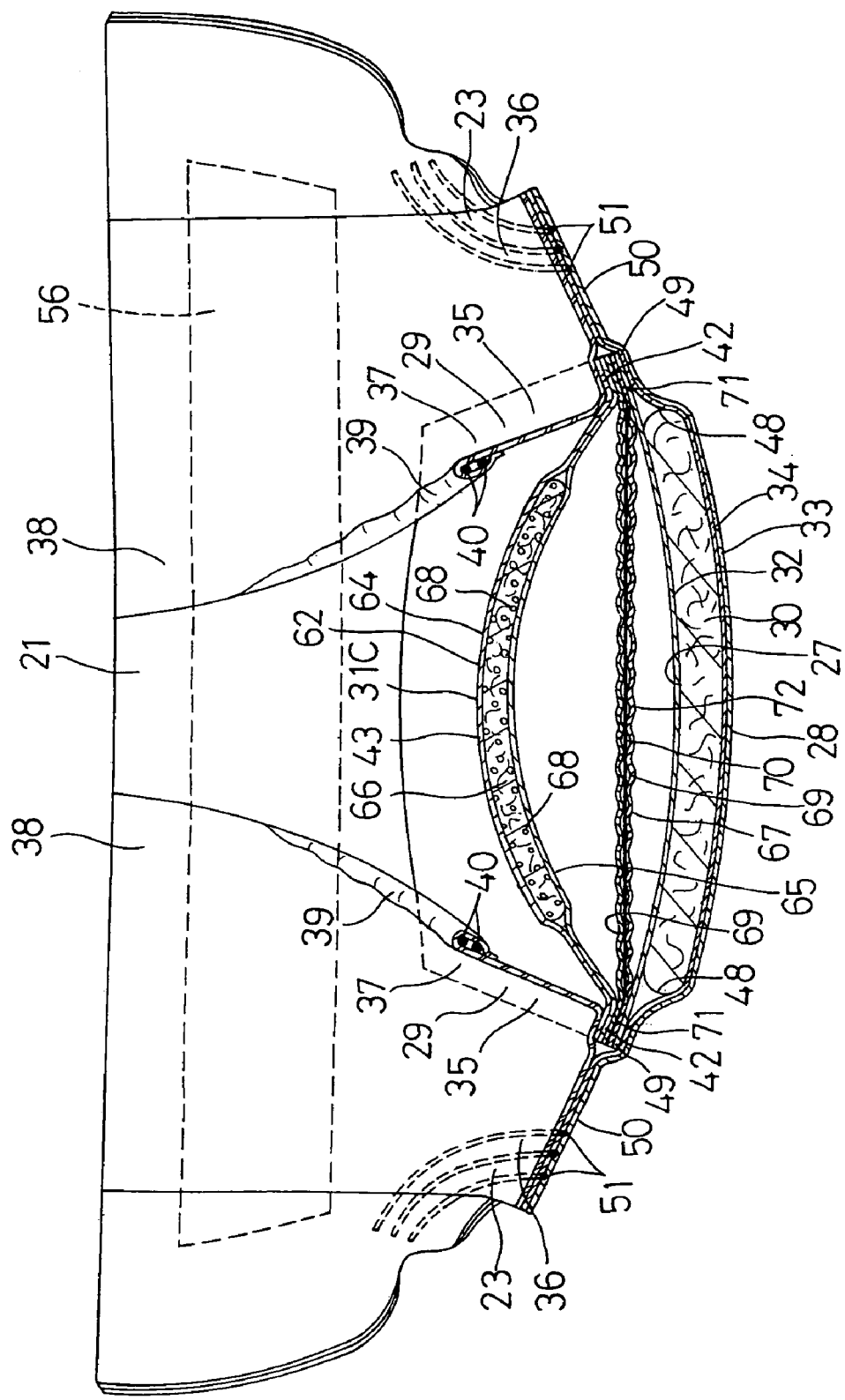
FIG. 11 is a sectional view taken along the line 11-11 in FIG. 9.

FIG. 9 is a perspective view showing a disposable article 20C as another preferred embodiment of the invention, FIG. 10 is a sectional view taken along the line 10-10 in FIG. 9 and FIG. 11 is a sectional view taken along the line 11-11 in FIG. 9. In FIG. 9, a transverse direction is indicated by an arrow L, a longitudinal direction is indicated by an arrow M and a thickness direction is indicated by an arrow N. As used herein the term "inner surfaces" of first and second fibrous nonwoven fabric layers 64, 65 refer to the respective surfaces thereof facing urethane foam 66 and the term "outer surfaces" thereof refer to the respective surfaces thereof facing away from the urethane foam 66.

The article 20C is similar to the article 20A except that the article 20C includes a partition 31C in place of the partition 31A and a spacer 67 interposed between the topsheet 27 and the partition 31C so as to extend in the transverse direction. The components similar to those in FIG. 1 are denoted by the same reference numerals and the description of the arrangements in the article 20C similar to those in FIGS. 1-4 is omitted here.

The partition 31C is of a rectangular shape which is relatively long in the transverse direction and laid in a front half of the crotch region 25 divided by the transverse centerline L1. The partition 31C comprises a body-faceable first hydrophilic nonwoven fabric layer 64 (which may be referred to as "water-pervious sheet"), an opposed second hydrophilic fibrous nonwoven fabric 65 (which may be referred to as "water-impervious sheet") and a urethane foam 66 ("which may be referred to as "absorbent core material") interposed between the first and second fibrous nonwoven fabric layers 64, 65. These nonwoven fabric layers 64, 65 have respective portions extending outward beyond a peripheral edge of the urethane foam 66 and placed upon and bonded to each other. The urethane foam 66 has a plurality of open cells 68 therein. The urethane foam 66 is intermittently bonded to the mutually opposing surfaces of these nonwoven fabric layers 64, 65 by means of adhesives (not shown). The absorbent core material is not limited to the urethane foam 66 and may be selected from the group consisting of a cellulose sponge, nylon sponge and styrene foam.

The partition 31C has a lateral zones 42 bonded to the side edges 23 of the article 20C and an intermediate zone 43 extending between these lateral zones 42 and left free from the article 20C. The lateral zones 42 are formed from the first and second fibrous nonwoven fabric layers 64, 65 except the urethane foam 66. The lateral zones 42 are interposed between the proximal zones 36 of the respective leak-barrier flaps 29 and lateral zones 71 of a spacer 67 which will be described later and bonded to them.

The spacer 67 is provided in the region 62 of the intermediate zone 43 (i.e., in the region placed aside toward the transverse centerline L1). The spacer 67 is formed from a pair of hydrophilic or hydrophobic fibrous nonwoven fabric layers 69 and a plurality of stretch- and contractable elastic members 70 attached in a stretched state to the fibrous nonwoven fabric layers 69. The elastic members 70 are interposed between these fibrous nonwoven fabric layers 69 and intermittently and secured with tension of a given stretching ratio in the transverse direction to the mutually opposing surfaces of these nonwoven fabric layers 69 by means of adhesives (not shown). The spacer 67 is attached with tension of a given stretching ratio in the transverse direction to the partition 31C. The spacer 67 has transversely opposite lateral zones 71 laid in the vicinity of the transversely opposite side edges 23 of the article 20C and a middle zone 72 extending between the lateral zones 71 and left free from both the article 20C and the partition 31C. The lateral zones 71 are interposed between the side edges 49 of the topsheet 27 and the lateral zones 42 of the partition 31C and bonded to the mutually opposing surfaces of them. The lateral zones 42 of the partition 31C are drawn near to each other in the transverse direction of the article 20C as the spacer 67 contracts so that the intermediate zone 43 of the partition 31C curves in the transverse direction so as to describe a generally circular arc which is convex upward above the topsheet 27.

Figure 12:
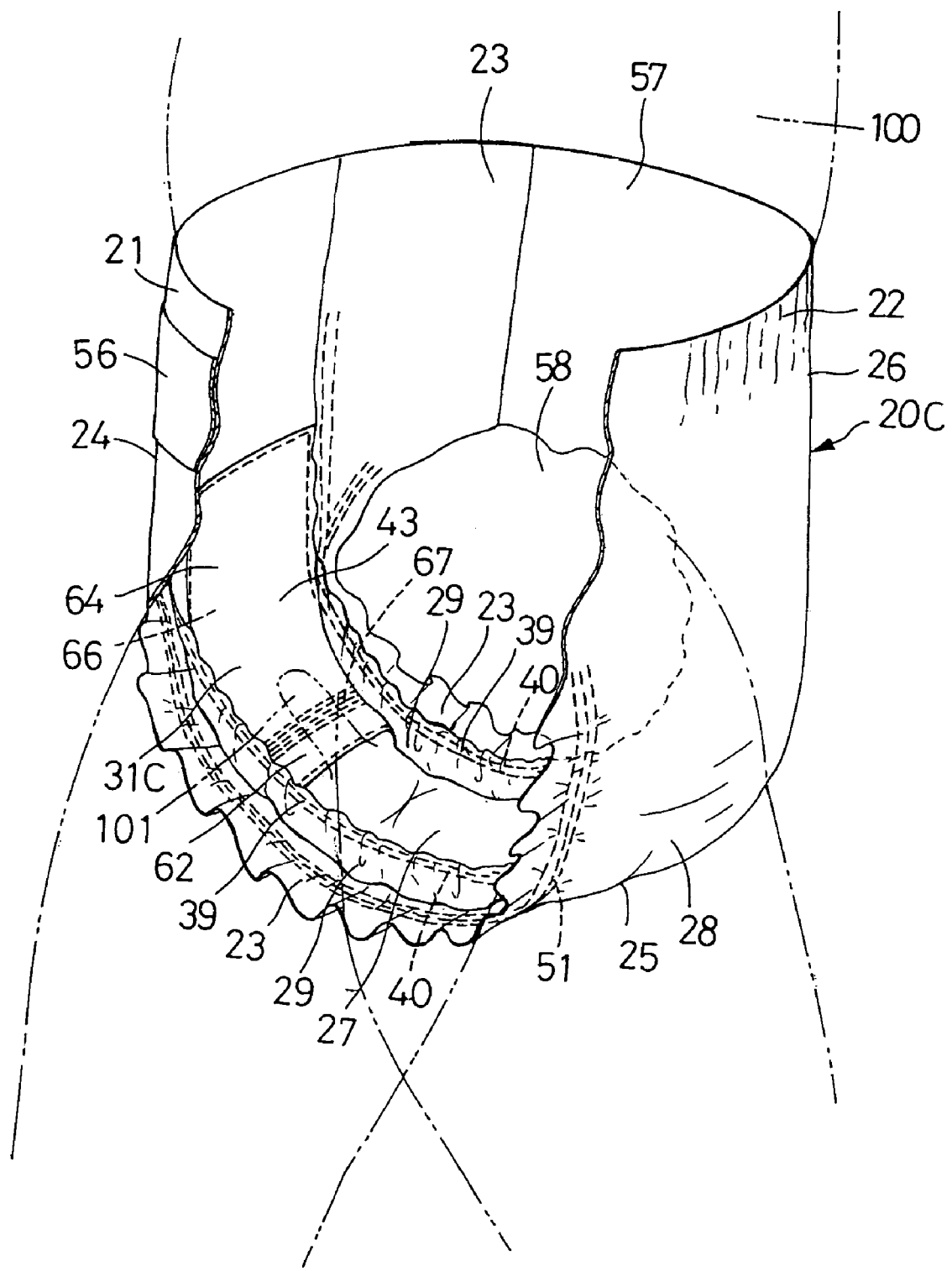
FIG. 12 is a perspective view showing the article of FIG. 9 as put on a wearer's body.

FIG. 12 is a perspective view showing the article 20C of FIG. 9 as worn, in which the side edges 23 of the front and rear waist regions 24, 26 are cut away on one side of the waist. Sequential procedures to put the article 20C on the wearer's body are the same as in the case of the article 20A shown in FIGS. 1-4 and the description thereof is omitted here. During use of the wearing article 20C, the buttock of the wearer 100 is in contact with the topsheet 27 and the penis 101 of the wearer 100 is in contact with the outer surface of the partition 31C. During use of the article 20C, the penis 101 of the wearer 100 comes in contact with the outer surface of the partition 31C but not in contact with the topsheet 27. Even if loose passage discharged onto the rear half of the crotch region 25 as well as onto the rear waist region 26 spreads on the topsheet 27 and moves toward the front half of the crotch region 25 and the front waist region 24, the partition 31C interposed between the topsheet 27 and the penis 101 prevents such loose passage from clinging to and soiling the penis 101.

The contractile force of the spacer 67 normally biases the intermediate zone 43 of the partition 31C to rise up so as to describe a generally circular arc which is convex upward above the topsheet 27. Therefore, the intermediate zone 43 reliably rises up in the shape of a generally circular arc above the topsheet 27 to be spaced upward spaced from the topsheet 27 as the crotch region 25 is squeezed between the wearer's thighs inward in the transverse direction during use of the article 20C. Therefore, consequently, any amount of loose passage can not transfer from the topsheet 27 to the partition 31C, and the penis 101 can be reliably protected from contamination with loose passage. Urine discharged is absorbed by the urethane foam 66 through the first fibrous nonwoven fabric layer 64 and contained therein while feces discharged are absorbed by the core 30 through the topsheet 27 and contained therein. It should be noted here that ever when the urethane foam 66 has absorbed urine, it does not lose its resiliency and therefore can support the wearer's penis 101 with the partition 31C spaced apart from the topsheet 27.

Figure 13:
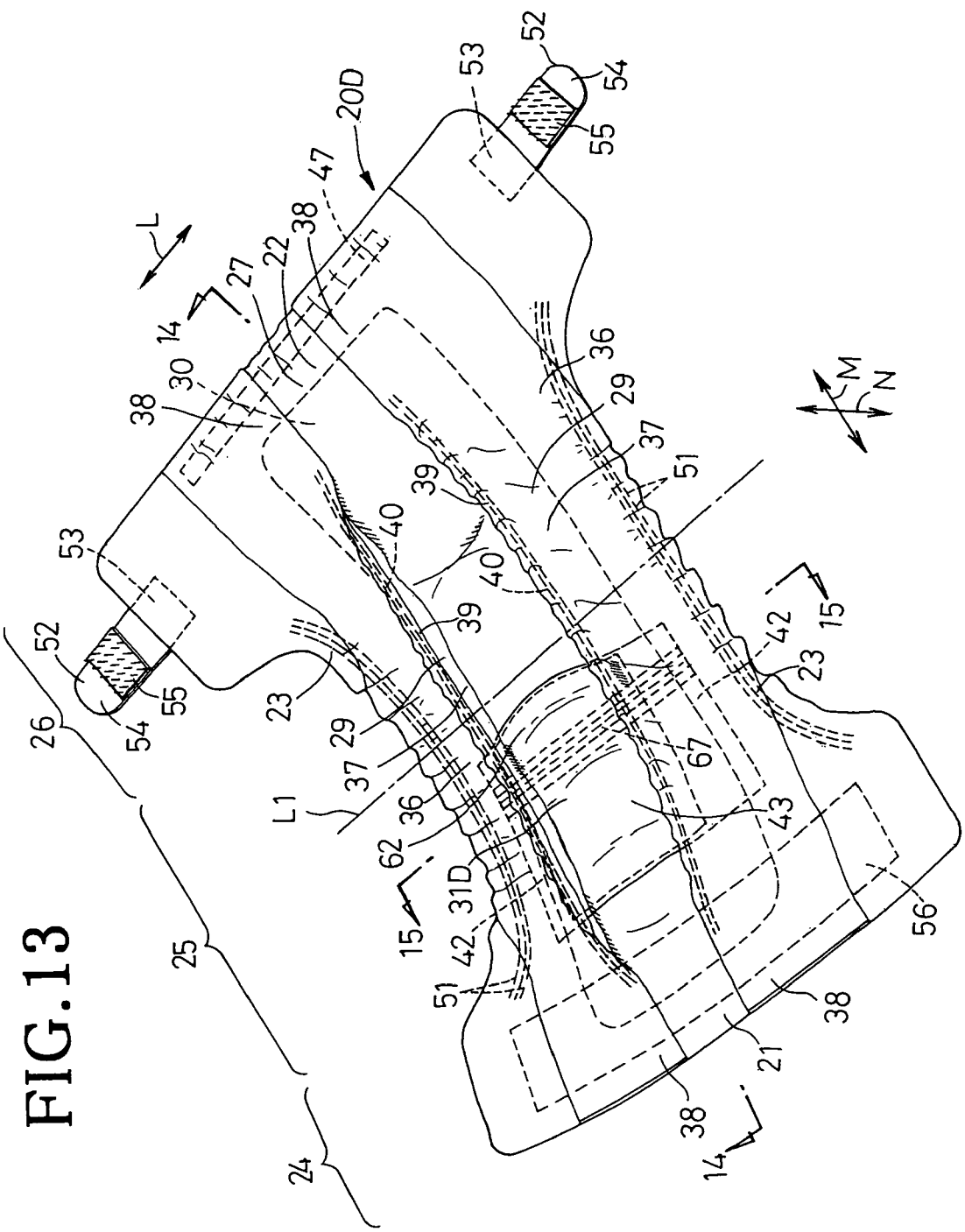
FIG. 13 is a partially cutaway perspective view showing still another preferred embodiment of the disposable wearing article according to the invention.
Figure 14:
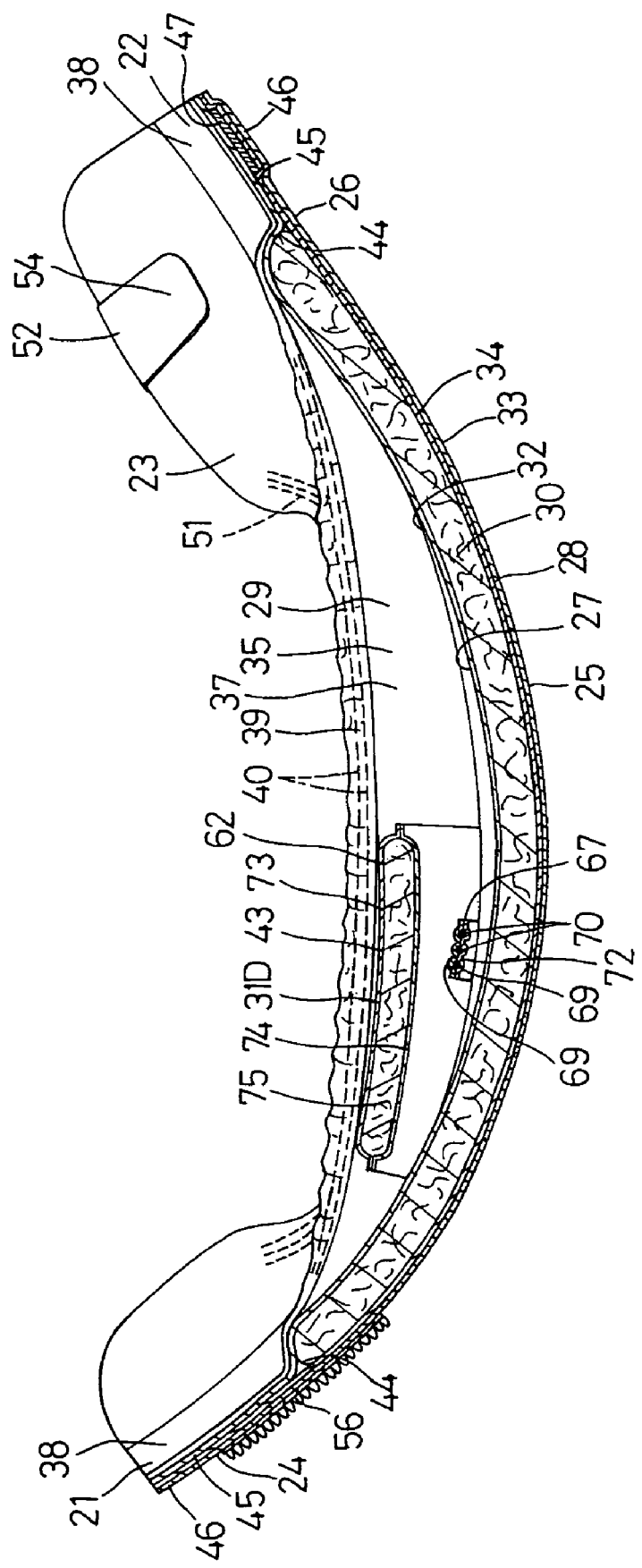
FIG. 14 is a sectional view taken along the line 14-14 in FIG. 13.
Figure 15:
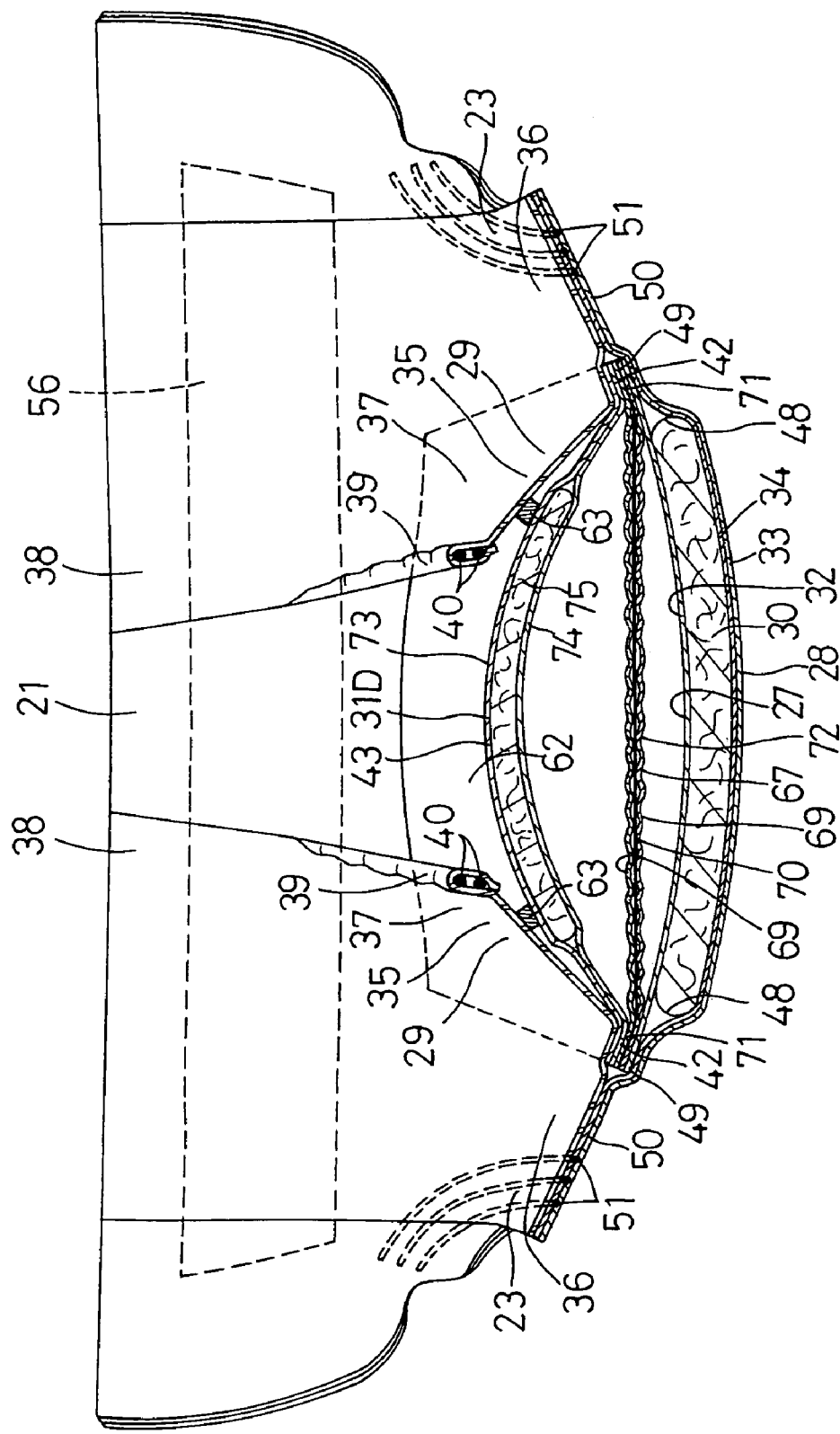
FIG. 15 is a sectional view taken along the line 15-15 in FIG. 13.

FIG. 13 is a perspective view showing a disposable article 20D as still another preferred embodiment of the invention, FIG. 14 is a sectional view taken along the line 14-14 in FIG. 13 and FIG. 15 is a sectional view taken along the line 15-15 in FIG. 13. In FIG. 13, a transverse direction is indicated by an arrow L, a longitudinal direction is indicated by an arrow M and a thickness direction is indicated by an arrow N. As used herein the term "inner surfaces" of nonwoven fabric 73 and film 74 refer to the respective surfaces thereof facing a core 75 and the term "outer surfaces" thereof refer to the respective surfaces thereof facing away from the core 75.

The article 20D is similar to the article 20A of FIGS. 1-4 except that the article 20D includes a partition 31D in place of the partition 31A and a spacer 67 is interposed between the topsheet 27 and the partition 31D so as to extend in the transverse direction. The components similar to those in the embodiment shown in FIGS. 1-4 are denoted by the same reference numerals and the description of the arrangement similar to that in the embodiment shown in FIGS. 1-4 is omitted here.

The partition 31D is of a rectangular shape which is relatively long in the transverse direction and laid in a front half of the crotch region 25 divided by the transverse centerline L1. The partition 31D comprises a body-faceable hydrophilic nonwoven fabric 73 (which may be referred to as "water-pervious sheet"), a wearer-opposing liquid-impervious plastic film 74 (which may be referred to as "water-impervious sheet") and a liquid-absorbent core 75 (which may be referred to as "absorbent core material") interposed between the nonwoven fabric 73 and the film 74. These nonwoven fabric 73 and film 74 have respective portions extending outward beyond a peripheral edge of the core 75 and placed upon and bonded to each other. In the partition 31D, the liquid-impervious plastic film 74 may be replaced by a hydrophobic fibrous nonwoven fabric or repellent treated hydrophobic fibrous nonwoven fabric. The core 75 is intermittently bonded to the mutually opposing surfaces of the nonwoven fabric 73 and the film 74 by means of adhesives (not shown). The core 75 is formed from the same mixture as the core 30 and entirely wrapped with a liquid-absorption and diffusion such as a tissue paper or hydrophilic fibrous nonwoven fabric or the like (not shown). The core 30 has a stiffness higher than those of the nonwoven fabric 73 and the film 74.

The partition 31D has transversely opposite lateral zones 42 bonded to the side edges 23 of the article 20D and an intermediate zone 43 extending between the lateral zones 42 and left free from the article 20D. The lateral zones 42 are formed from the nonwoven fabric 73 and the film 74 except the core 75. The lateral zones 42 are interposed between the side edges 36 of the leak-barrier flaps 29 and the lateral zones 71 of the spacer 67 and bonded to them. The intermediate zone 43 has a region 62 placed aside toward the transverse centerline L1 and bonded at both sides of this region 62 to the distal zones 37 of the respective leak-barrier flaps 29 in the vicinity of the elastic members 40 (more specifically, in the vicinity of the distal edges 39). Without departing from the scope of the invention, the intermediate zone 43 may be bonded along the full length thereof to the zones 37 of the respective leak-barrier flaps 29 in the vicinity of the elastic members 40.

Figure 16:
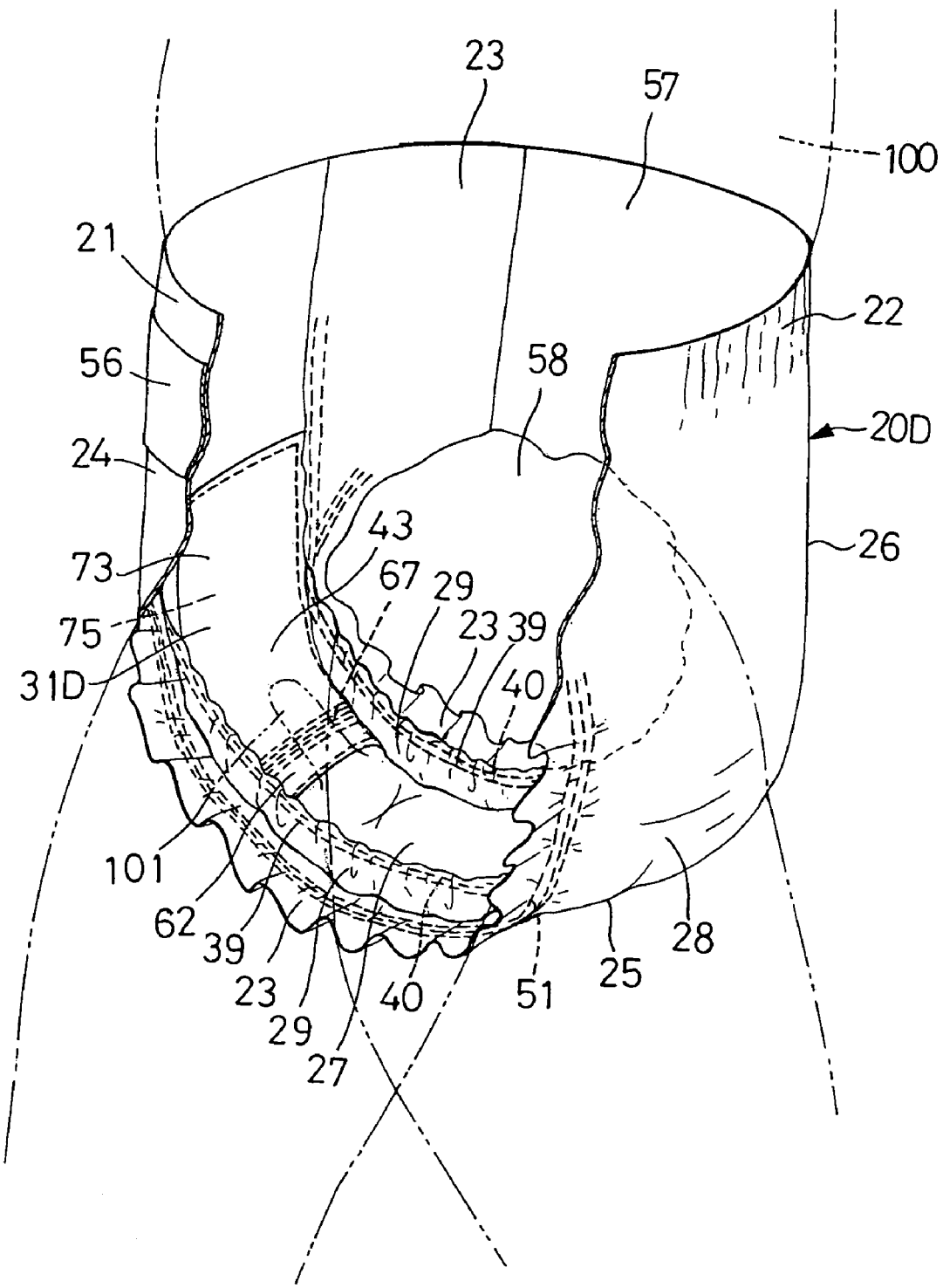
FIG. 16 is a perspective view showing the article of FIG. 13 as put on a wearer's body.

FIG. 16 is a perspective view showing the article 20D of FIG. 16 as worn, in which the side edges 23 of the front and rear waist regions 24, 26 are cut away on one side of the waist. Sequential procedures to put the article 20D on the wearer's body are the same as in the case of the article 20A shown in FIGS. 1-4 and the description thereof is omitted here. During use of the wearing article 20D, the buttock of the wearer 100 is in contact with the topsheet 27 and the penis 101 of the wearer 100 is in contact with the outer surface of the partition 31D.

The article 20D ensures that urine discharged is absorbed by the core 75 through the fibrous nonwoven fabric 73 and even a large amount of urine can be reliably absorbed by the partition 31D. In this way, there is unlikely that because this article 20D can prevent such urine from permeating the film 74 and reaching the topsheet 27, the article 20D can prevent feces from being unacceptably fluidized due to commingling with urine and thereby protect the skin of the wearer 100 from soiling with such excessively fluidized feces.

Figure 17:
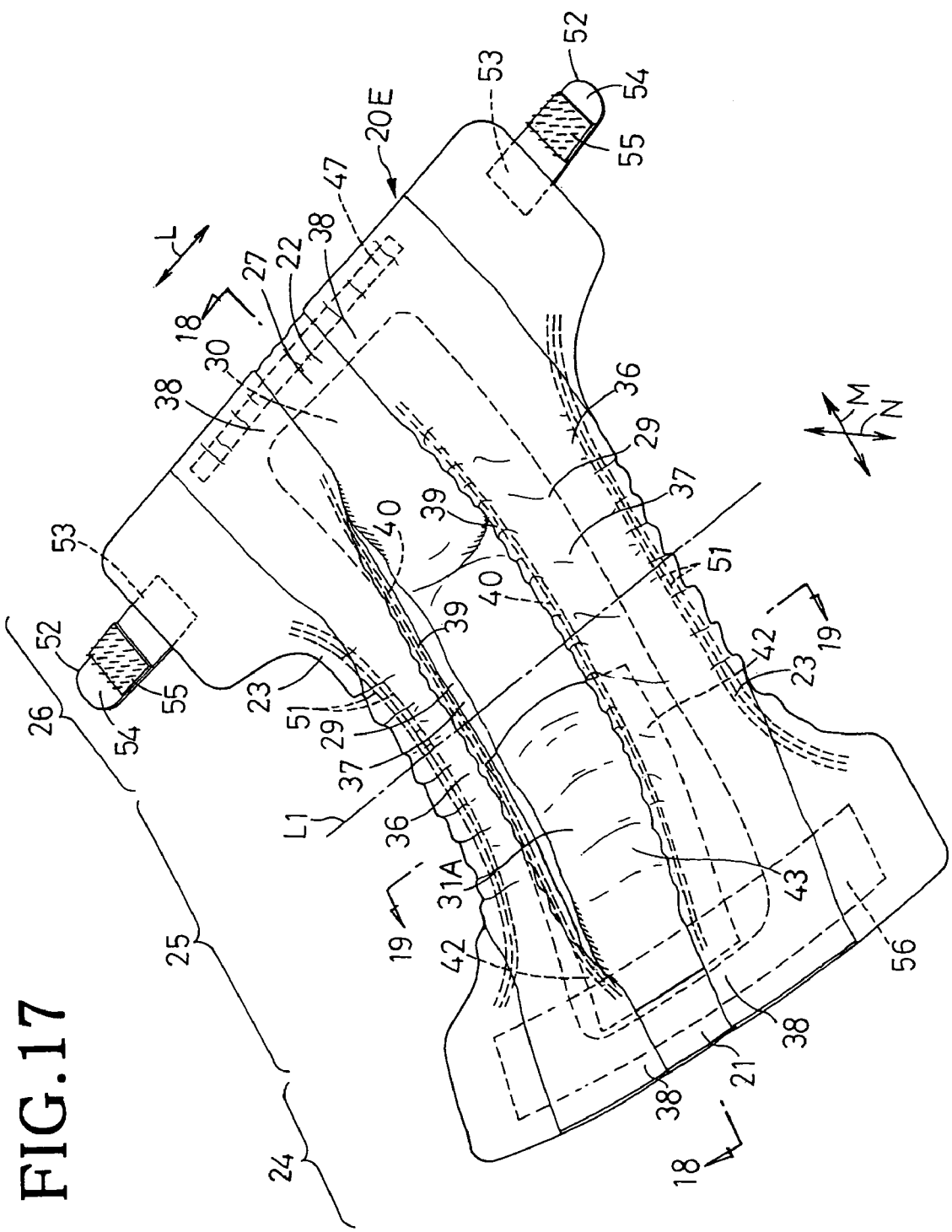
FIG. 17 is a partially cutaway perspective view showing further another preferred embodiment of the disposable wearing article according to the invention.
Figure 18:
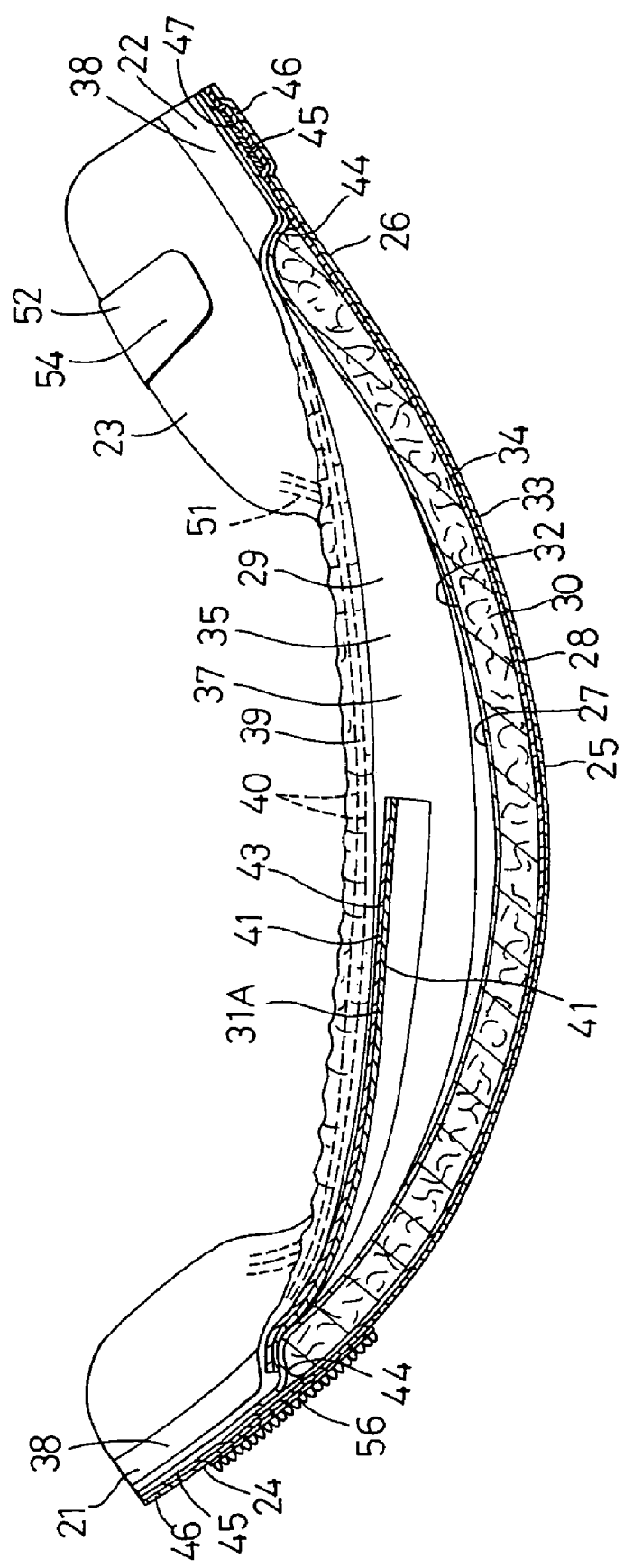
FIG. 18 is a sectional view taken along the line 18-18 in FIG. 17.
Figure 19:
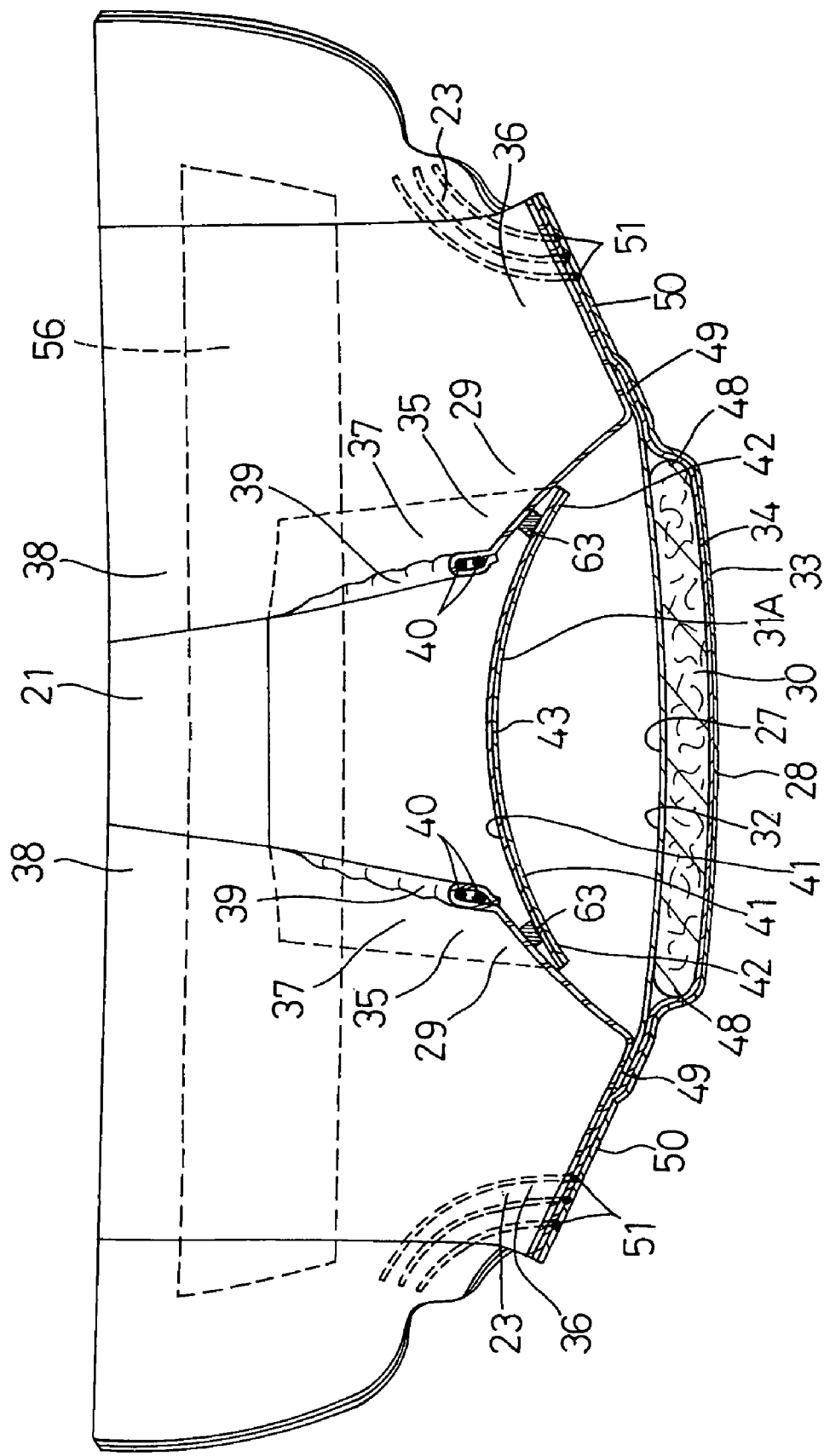
FIG. 19 is a sectional view taken along the line 19-19 in FIG. 17.
Figure 20:
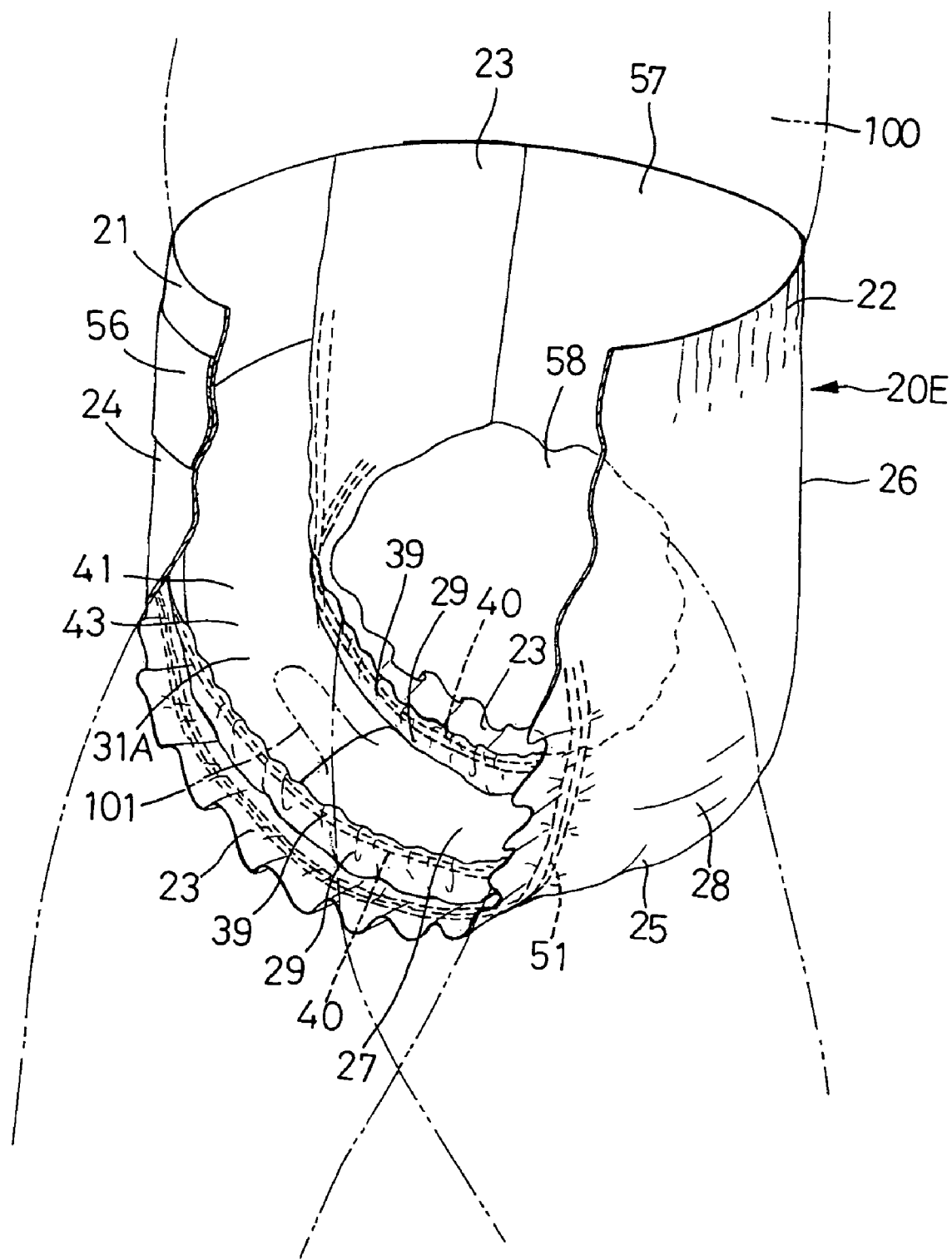
FIG. 20 is a perspective view showing the article of FIG. 17 as put on a wearer's body.

FIG. 17 is a perspective view showing a disposable wearing article 20E as further another preferred embodiment of the invention, FIG. 18 is a sectional view taken along the line 18-18 in FIG. 17 and FIG. 19 is a sectional view taken along the line 19-19 in FIG. 17. In FIG. 17, a transverse direction is indicated by an arrow L, a longitudinal direction is indicated by an arrow M and a thickness direction is indicated by an arrow N. FIG. 20 is a perspective view showing the article 20E of FIG. 17 as worn, in which the front and rear waist regions 31, 33 are illustrated as partially cutaway on one side of the waist.

This article 20E is similar to the article 20A of FIGS. 1-4 except that the lateral zones 42 of the partition 31A are bonded to the zones 37 of the respective leak-barrier flaps 29 and the partition 31A extends over the front waist region 24 and a front half of the crotch region 25. The components similar to those in the embodiment shown in FIGS. 1-4 are denoted by the same reference numerals and the description of the arrangement similar to that in the embodiment shown by FIGS. 1-4 is omitted here.

The partition 31A is laid in a rear half of the front waist region 24 and a front half of the crotch region 25 divided by the transverse centerline L1 and thereby urine can be absorbed by the partition 31A in a more wide-range. The lateral zones 42 of the partition 31A are bonded to the distal zone 37 of the leak-barrier flaps 29 and thereby the lateral zones 42 and the intermediate zone 43 are raised up above the topsheet 27 and spaced upward from the topsheet 27 as the distal zones 37 of the respective leak-barrier flaps 29 rise up. Consequently, the intermediate zone 43 of the partition 31A curves in the transverse direction so as to describe a generally arc which is convex upward above the distal edges 39 of the respective leak-barrier flaps 29, and the intermediate zone 43 is spaced upward from the topsheet 27 sufficiently to prevent loose passage from permeating the intermediate zone 43 and the penis 101 is reliably protected from soiling with loose passage.

Stock materials for the topsheet 27 is not limited to the hydrophilic fibrous nonwoven fabric but may be also selected from the group consisting of a hydrophobic fibrous nonwoven fabric having a plurality of perforations and a plastic film having a plurality of fine apertures. Stock materials for the backsheet 28 is not limited to the composite nonwoven fabric but may be selected from the group consisting of a hydrophobic fibrous nonwoven fabric and a breathable liquid-impervious plastic film. It is possible without departing from the scope of the invention to form the backsheet 28 and the leak-barrier flaps 29 using a composite nonwoven fabric (SM nonwoven fabric, SMS nonwoven fabric or SMMS nonwoven fabric) consisting of a melt blown fibrous nonwoven fabric having a high water-resistance and a spun bond fibrous nonwoven fabric being high in strength as well as in flexibility laminated on at least one side of the melt blown fibrous nonwoven fabric.

Stock materials for the fibrous nonwoven fabric layers may be selected from the group consisting of spun lace-, needle punch-, melt blown-, thermal bond-, spun bond- and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fiber selected from the group consisting of core-sheath conjugate fibers, side-by-side conjugate fibers, modified macaroni fibers, microporous fibers and fused type conjugate fibers.

Bonding of the top- and backsheets 27, 28 to each other, bonding of the sheets 27, 28 to the leak-barrier flaps 29, bonding of the core 30 to the sheets 27, 28, bonding of the partition 31A, 31B, 31C, 31D to the sheets 27 and the flaps 29 and bonding of the elastic members 40, 47, 51 to the sheets 27, 28 and the flaps 29 may be achieved by using adhesives or welding technique such as heat-sealing or sonic sealing. Adhesives may be selected from the group consisting of a hot melt adhesive, an acrylic adhesive and a rubber-based adhesive.

The adhesives are coated on the topsheet 27, the backsheet 28 and the leak-barrier flaps 29 preferably in anyone of a spiral, wavy, zigzag, dotted or striped pattern. These sheets 27, 28 and the flaps 29 may be coated with adhesives in such patterns to define adhesive-coated regions and adhesive-free regions in these sheets 27, 28 and the flaps 29 and thereby to ensure that these sheets 27, 28 and the flaps 29 are intermittently bonded one to another, the core 29 is intermittently bonded to the sheets 27, 28 and the elastic members 40, 47, 51 are intermittently bonded to the sheets 27, 28 and the flaps 29.

In the articles 20A, 20E, respectively, the partition 31A may be replaced by any one of the partitions 31B, 31C and 31D, respectively. In the article 20B, the partition 31B may be replaced by any one of the partitions 31A, 31C and 31D, respectively. In the article 20C, the partition 31C may be replaced by any one of the partitions 31A, 31B and 31D, respectively. In the article 20D, the partition 31D may be replaced by any one of the partitions 31A, 31B and 31C. In the articles 20A, 20B, 20C and 20D, it is also possible to lay the partitions 20A, 20B, 20C and 20D, respectively, in the front half of the crotch region 25 and in the front waist region 24. In the article 20E, it is also possible to lay the partition 31A in the front half of the crotch region 25 alone.

In the articles 20A and 20C, respectively, it is also possible to eliminate the leak-barrier flaps 29 from the opposite side edges 23. When it is desired to construct the article 20A in this manner, the lateral zones 42 of the partition 31 may be bonded to the inner surface of the side edges 49 of the topsheet 27. When it is desired to construct the article 20C in this manner, the lateral zones 42 of the partition 31 may be bonded to the lateral zones 71 of the spacer 67.

What is claimed is:

1. A disposable wearing article, comprising:
a diaper structure which includes
a front waist region;
a rear waist region;
a crotch region extending in a longitudinal direction of the article between said front and rear waist regions;
a body-faceable liquid-pervious topsheet;
an opposed liquid-impervious backsheet;

a liquid-absorbent core interposed between said topsheet and said backsheet so as to extend between said front and rear waist regions;

a partition which extends in a transverse direction of said article above said topsheet and is positioned at least in a front half of the crotch region, said partition having transversely opposite lateral zones bonded to transversely opposite side edge portions of the diaper structure and an intermediate zone defined between said lateral zones and free of direct attachment to said diaper structure; and a pair of leak-barrier flaps extending in the longitudinal direction of said article above the topsheet, said leak-barrier flaps having proximal zones bonded to the side edge portions of said diaper structure so as to extend in the longitudinal direction, distal zones extending in the longitudinal direction and biased to rise up above said topsheet, front and rear ends collapsed in the transverse direction and bonded in such collapsed state to vicinities of front and rear ends of said diaper structure, and stretchable and contractible elastic members attached in a stretched state to said distal zones;

wherein said partition is laid between said leak-barrier flaps and has transversely opposite regions of said intermediate zone being permanently and directly bonded to the respective distal zones of said leak-barrier flaps so that said intermediate zone is lifted above said topsheet as the respective distal zones of said leak-barrier flaps rise up above said topsheet;

a channel is defined between the intermediate zone of said partition and said topsheet to allow free movement of body discharges in the longitudinal direction between the front and rear waist regions;

the lateral zones of said partition are bonded to the respective side edge portions of the diaper structure at first bonding sites; and the transversely opposite regions of said intermediate zone are permanently and directly bonded to the respective distal zones of said leak-barrier flaps at second bonding sites which are different from and located between the first bonding sites as seen in the transverse direction.

\* \* \* \* \*